(12) United States Patent
Cheng et al.

(10) Patent No.: US 7,747,301 B2
(45) Date of Patent: Jun. 29, 2010

(54) APPARATUS AND METHOD FOR NON-INVASIVE AND MINIMALLY-INVASIVE SENSING OF PARAMETERS RELATING TO BLOOD

(75) Inventors: Xuefeng Cheng, Cupertino, CA (US); Daniel Hwan Kim, Mountain View, CA (US); Butrus T. Khuri-Yakub, Palo Alto, CA (US)

(73) Assignee: Skyline Biomedical, Inc., Los Altos, CA (US)

( * ) Notice: Subject to any disclaimer, the term of this patent is extended or adjusted under 35 U.S.C. 154(b) by 846 days.

(21) Appl. No.: 11/233,308

(22) Filed: Sep. 22, 2005

(65) Prior Publication Data

US 2006/0253007 A1 Nov. 9, 2006

(51) Int. Cl.
*A61B 5/145* (2006.01)
(52) U.S. Cl. ........................... 600/322; 600/407
(58) Field of Classification Search .................. 600/323, 600/324, 333, 338, 407, 437
See application file for complete search history.

(56) References Cited

U.S. PATENT DOCUMENTS

| | | | | |
|---|---|---|---|---|
| 5,924,979 A * | 7/1999 | Swedlow et al. | ............. | 600/300 |
| 5,951,481 A * | 9/1999 | Evans | .......................... | 600/473 |
| 6,256,523 B1 * | 7/2001 | Diab et al. | ................... | 600/323 |
| 6,334,065 B1 * | 12/2001 | Al-Ali et al. | ................. | 600/323 |
| 6,397,092 B1 * | 5/2002 | Norris et al. | ................. | 600/323 |
| 6,397,099 B1 * | 5/2002 | Chance | ........................ | 600/473 |
| 6,456,862 B2 * | 9/2002 | Benni | .......................... | 600/331 |
| 6,498,942 B1 * | 12/2002 | Esenaliev et al. | ........... | 600/310 |
| 6,690,958 B1 * | 2/2004 | Walker et al. | ................ | 600/323 |
| 6,738,653 B1 * | 5/2004 | Sfez et al. | .................... | 600/322 |
| 6,805,673 B2 * | 10/2004 | Dekker | ........................ | 600/529 |
| 6,819,950 B2 * | 11/2004 | Mills | ........................... | 600/322 |
| 6,904,302 B2 * | 6/2005 | Hirabayashi et al. | ........ | 600/344 |
| 2004/0116789 A1 * | 6/2004 | Boas et al. | .................... | 600/338 |
| 2004/0267104 A1 * | 12/2004 | Hannula et al. | .............. | 600/340 |
| 2005/0038344 A1 * | 2/2005 | Chance | ........................ | 600/473 |

* cited by examiner

*Primary Examiner*—Eric F Winakur
*Assistant Examiner*—Etsub D Berhanu
(74) *Attorney, Agent, or Firm*—Patterson & Sheridan, LLP

(57) ABSTRACT

Medical diagnostic system, apparatus and methods are disclosed. Optical transmitters generate radiation-containing photons having a specific interaction with at least one target chromophore in a target structure, preferably a blood vessel such as the interior jugular vein. The optical transmitters transmit the radiation into at least a first area including a substantial portion of the target structure and into a second area not including a substantial portion of the target structure. Optical receivers detect a portion radiation scattered from at least the first area and the second area. A processor estimates oxygenation, pH or cardiac output based on the scattered radiation detected from the first area, and the scattered radiation from the second area.

72 Claims, 23 Drawing Sheets

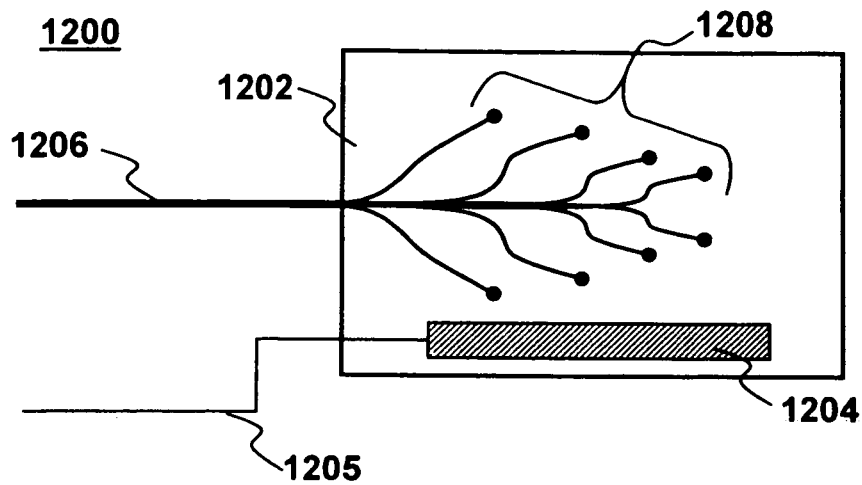
FIG. 12A
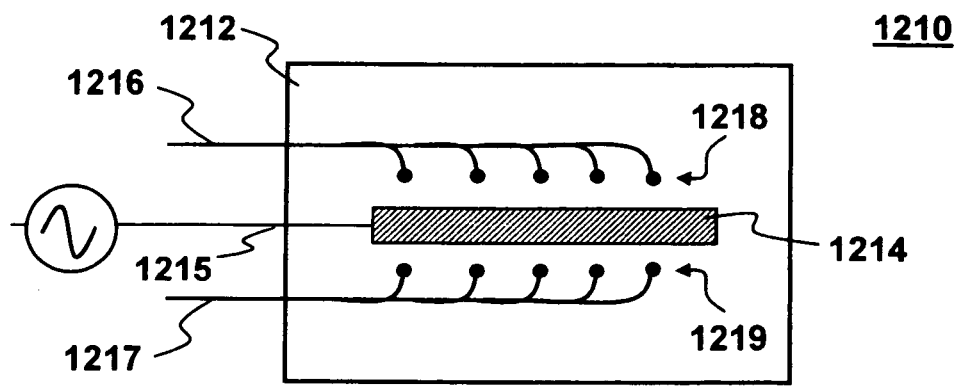
FIG. 12B
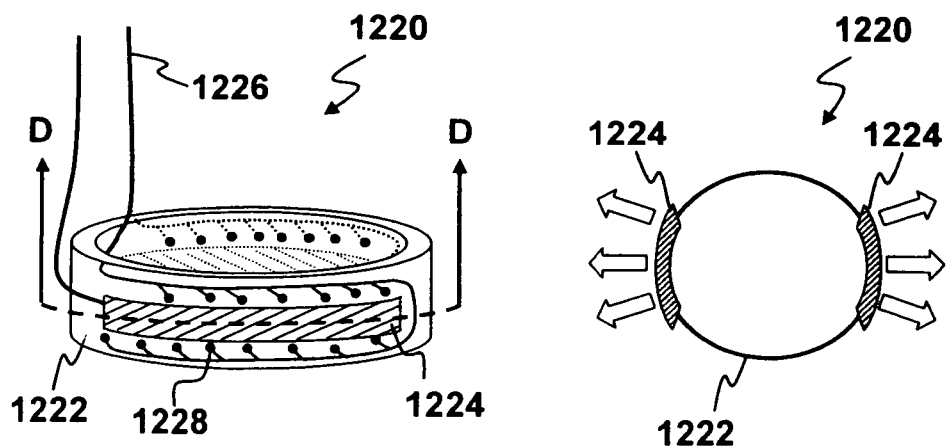
FIG. 12C  FIG. 12D

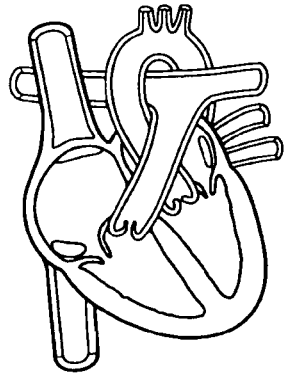
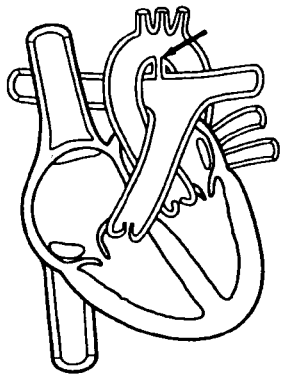
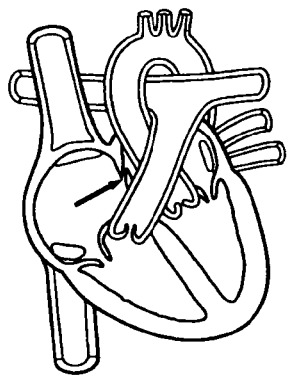
FIG. 18A  FIG. 18B  FIG. 18C
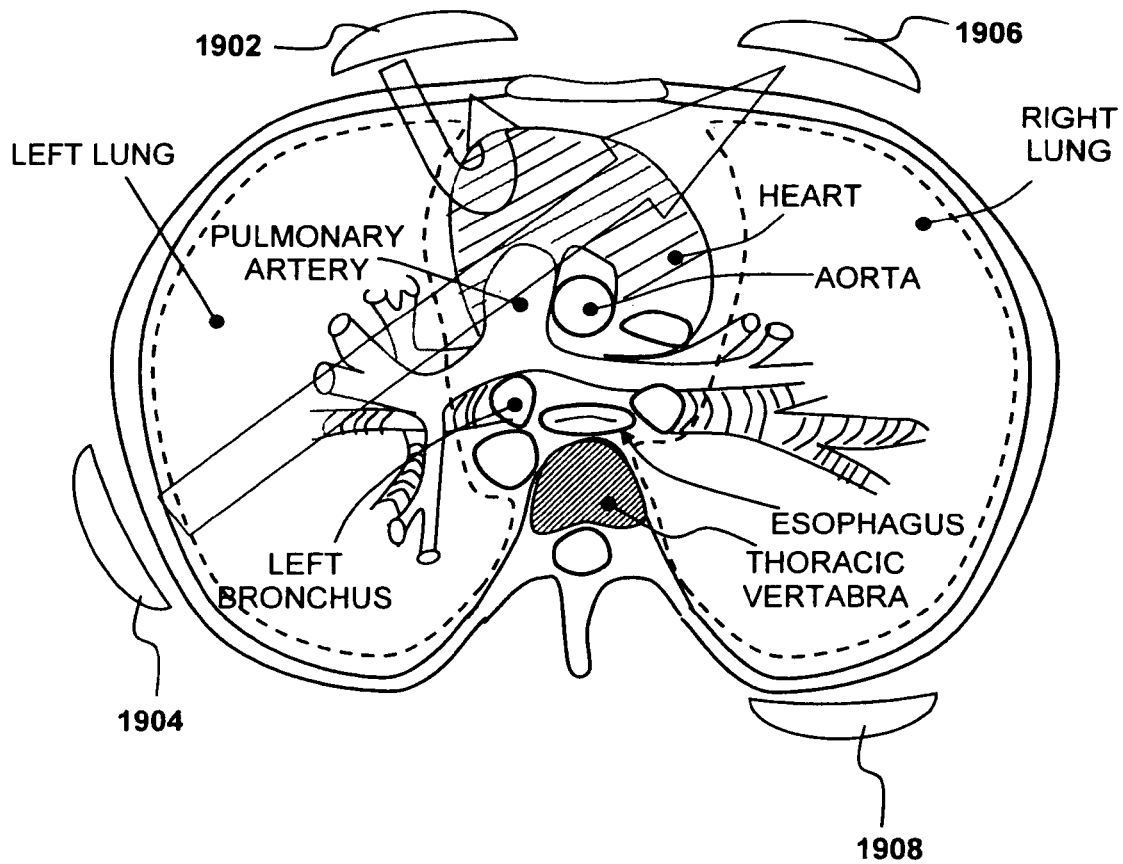
FIG. 19

APPARATUS AND METHOD FOR NON-INVASIVE AND MINIMALLY-INVASIVE SENSING OF PARAMETERS RELATING TO BLOOD

CROSS-REFERENCE TO RELATED APPLICATION

This application is related to co-pending U.S. patent application Ser. No. 11/095,091, filed 30 Mar. 2005, in the name of John F. Black, Daniel Hwan Kim, and Butrus T. Khuri-Yakub, entitled, "Apparatus and Method for Non-Invasive and Minimally-Invasive Sensing of Venous Oxygen Saturation and pH Levels", which is hereby incorporated by reference as if fully set forth herein.

FIELD OF THE INVENTION

This invention is related to techniques for monitoring vital bodily functions, including cardiac output. It relates in particular to methods and apparatus for non-invasive and minimally-invasive real-time monitoring of parameters such as venous oxygenation saturation or pH in a vessel, an organ or tissue containing blood.

BACKGROUND OF THE INVENTION

Cardiac output is defined as the volume of blood circulated per minute. It is equal to the heart rate multiplied by the stroke volume (the amount ejected by the heart with each contraction). Cardiac output averages approximately 5 liters per minute for an average adult at rest, although it may reach up to 30 liters/minute during extreme exercise.

Cardiac output is of central importance in the monitoring of cardiovascular health, as discussed by Conway "Clinical assessment of cardiac output", Eur. Heart J. 11, 148-150 (1990). Accurate clinical assessment of the circulatory status is particular desirable in critically ill patients in the ICU and patients undergoing cardiac, thoracic, or vascular interventions, and has proven valuable in long term follow-up of outpatient therapies. As the patient's hemodynamic status may change rapidly, continuous monitoring of cardiac output will provide information allowing rapid adjustment of therapy. Measurements of cardiac output and blood pressure can also be used to calculate peripheral resistance.

A recent review of the various techniques for measuring cardiac output is given in Linton and Gilon, "Advances in non-invasive cardiac output monitoring", Annals of Cardiac Anaesthesia, 2002, volume 5, p 141-148. This article lists both non/minimally invasive and invasive methods and compares the advantages and disadvantages of each.

The pulmonary artery catheter (PAC) thermodilution method is generally accepted as the clinical standard for monitoring cardiac output, to which all other methods are compared as discussed by Conway and Lund-Johansen ("Thermodilution method for measuring cardiac output", Europ. Heart J. 11(Suppl 1), 17-20 (1990)). The long history of use has defined the technology, suitable clinical applications, and its inadequacies. Many new methods have attempted to replace the thermodilution technique, but none have so far gained acceptance.

Jansen (J. R. C. Jansen, "Novel methods of invasive/non-invasive cardiac output monitoring", Abstracts of the 7th annual meeting of the European Society for Intravenous Anesthesia, Lisbon 2004) describes eight desirable characteristics for cardiac output monitoring techniques; accuracy, reproducibility or precision, fast response time, operator independency, ease of use, continuous use, cost effectiveness, and no increased mortality and morbidity. A brief description of some of these techniques follows.

Indicator dilution techniques. There are several indicator dilution techniques including transpulmonary thermodilution (also known as PiCCO technology, from Pulsion Medical Technologies of Munich, Germany), transpulmonary lithium dilution method (LiDCO Group plc of London, UK), PAC based thermodilution and other methods (Vigilance, Baxter; Opti-Q, Abbott; and TruCCOMS, AorTech). U.S. Pat. No. 6,757,544 to Rubinstein et al. teaches the technique of optically monitoring indicator dilution in a non-invasive manner for the purpose of computation of cardiac output, cardiac index, and blood volume. Transpulmonary indicator dilution methods with bolus injections are variations on the conventional bolus thermodilution method. CO is calculated with use of the Steward-Hamilton equation (Geddes, "Cardiac output using the saline dilution impedance technique", IEEE Engineering in Medicine and Biology magazine March 1989, 22-26). Application of this equation assumes three major conditions; complete mixing of blood and indicator, no loss of indicator between place of injection and place of detection, and constant blood flow. The errors associated with indicator dilution techniques are primarily related to the violation of these conditions, as discussed by Lund-Johansen ("The dye dilution method for measurement of cardiac output", Europ. Heart J. 11 (Suppl 1), 6-12 (1990)) and de Leeuw and Birkenhager ("Some comments of the usefulness of measuring cardiac output by dye dilution", Europ. Heart J. 11 (Suppl 1), 13-16 (1990)). Of the mentioned methods the transpulmonary indicator dilution methods as well as the so-called 'continuous cardiac output' thermodilution methods have been partially accepted in clinical practice as described in, for example, Rödig et al. "Continuous cardiac output measurement: pulse contour versus thermodilution technique in cardiac surgical patients". Br J Anaesth 1999; 50: 525.

Fick principle. The direct oxygen Fick approach is currently the standard reference technique for cardiac output measurement, as discussed by Keinanen et al., "Continuous measurement of cardiac output by the Fick principle: Clinical validation in intensive care", Crit Care Med 20(3), 360-365 (1992), and Doi et al., "Frequently repeated Fick cardiac output measurements during anesthesia", J. Clin. Monit. 6, 107-112 (1990). It is generally considered the most accurate method currently available, although there are many possibilities of introducing errors, and considerable care is needed. However when using the Fick method to trend cardiac output over a short time interval, i.e. during an operation or in an intensive care unit stay, many of these sources of errors are no longer pertinent. The NICO (Novametrix) system is a non-invasive device that applies Fick's principle on $CO_2$ and relies solely on airway gas measurement as described by Botero et al., "Measurement of cardiac output before and after cardiopulmonary bypass: Comparison among aortic transit-time ultrasound, thermodilution, and noninvasive partial $CO_2$ rebreathing", J. Cardiothoracic. Vasc. Anesth. 18(5) 563-572 (2004). The method calculates effective lung perfusion, i.e. that part of the pulmonary capillary blood flow that has passed through the ventilated parts of the lung. The effects of unknown ventilation/perfusion inequality in patients may explain why the performance of this method shows a lack of agreement between thermodilution and $CO_2$-rebreathing cardiac output as described in Nielsson et al. al "Lack of agreement between thermodilution and $CO_2$-rebreathing cardiac output" Acta Anaesthesiol Scand 2001; 45:680.

Bio-Impedance and conduction techniques. The bio-impedance method was developed as a simple, low-cost method that gives information about the cardiovascular system and/or (de)-hydration status of the body in a non-invasive way. Over the years, a diversity of thoracic impedance measurement systems have also appeared. These systems determine CO on a beat-to-beat time base. Studies have been reported with mostly poor results, but in exceptional cases good correlations compared to a reference method. Many of these studies refer to the poor physical principles of the thoracic impedance method as described in Patterson "Fundamentals of impedance cardiography", IEEE Engineering in Medicine and Biology 1989; 35 to explain the discrepancies. The accuracy of this technique is increased when the electrodes are placed directly in the left ventricle, rather than on the chest, however this also increases its invasiveness.

Echo-Doppler ultrasound. This technique uses ultrasound and the Doppler effect to measure cardiac output. The blood velocity through the aorta causes a 'Doppler shift' in the frequency of the returning ultrasound waves. Echo-Doppler probes positioned inside the esophagus with their echo window on the thoracic aorta may be used for measuring aortic flow velocity, as discussed by Schmidlin et al, "Transoesophageal echocardiography in cardiac and vascular surgery: implications and observer variability", Brit. J. Anaesth. 86(4), 497-505 (2001). Aortic cross sectional area is assumed in devices such as the CardioQ, made by Deltex Medical PLC, Chichester, UK) or measured simultaneously as for example in the HemoSonic device made by Arrow International. With these minimally invasive techniques what is measured is aortic blood flow, not cardiac output. A fixed relationship between aortic blood flow and cardiac output is assumed. CO can therefore be calculated using this relationship. Abrupt changes in cardiac output are better followed with Doppler systems than with the PAC based continuous cardiac output systems as described in Roeck et al. "Change in stroke volume in response to fluid challenge: assessment using esophageal Doppler", Intensive Care Med 2003; 29:1729. This measurement requires an above average level of skill on the part of the operator of the ultrasound machine to get accurate reliable results.

Arterial pulse contour analysis. The estimation of cardiac output based on pulse contour analysis is an indirect method, since cardiac output is not measured directly but is computed from a pressure pulsation on basis of a criterion or model. The origin of the pulse contour method for estimation of beat-to-beat stroke volume goes back to the Windkessel model as described in, for example, Manning et al. "Validity and reliability of diastolic pulse contour analysis (Windkessel model) in humans", Hypertension. 2002 May; 39(5):963-8. Most pulse contour methods are based on this model explicitly or implicitly as described in Rauch et al. "Pulse contour analysis versus thermodilution in cardiac surgery", Acta Anaesthesiol Scand 2002; 46:424, Linton et al. "Estimation of changes in cardiac output from arterial blood pressure waveform in the upper limb", Br J Anaesth 2001; 86:486 and Jansen et al. "A comparison of cardiac output derived from the arterial pressure wave against thermodilution in cardiac surgery patients" Br J Anaesth 2001; 87:212.

Arterial pulse contour analysis techniques relate an arterial pressure or pressure difference to a flow or volume change. Three pulse contour methods are currently available; PiCCO (Pulsion), PulseCO (LiDCO) and Modelflow (TNO/BMI). All three of these pulse contour methods use an invasively measured arterial blood pressure and they need to be calibrated. PiCCO is calibrated by transpulmonary thermodilution, LiDCO by transpulmonary lithium dilution and Modelflow by the mean of 3 or 4 conventional thermodilution measurements equally spread over the ventilatory cycle. Output of these pulse contour systems is calculated on a beat-to-beat basis, but presentation of the data is typically within a 30-second window. A non-invasive pulse contour development is the combination of non-invasively measured arterial finger blood pressure with Modelflow as described in Hirschl et al. "Noninvasive assessment of cardiac output in critically ill patients by analysis of finger blood pressure waveform", Crit Care Med 1997; 25:1909.

None of the above-mentioned CO techniques combines all of the eight "Jansen" criteria mentioned above. With respect to accuracy and precision, a number of methods may approach the thermodilution method with a precision of 15%. None of these new techniques has displaced conventional thermodilution based on the averaged result of 3 or 4 measurements done equally spread over the ventilatory cycle as described in Jansen et al. "An adequate strategy for the thermodilution technique in patients during mechanical ventilation", Intensive Care Med 1990; 16:422. Under research conditions the use of this conventional thermodilution method remains the method of choice. However, in clinical settings, the lower precision of the continuous cardiac output techniques may be outweighed by their advantages of being automatic and continuous.

In addition to measuring cardiac output, it is also desirable in many critical care situations to continuously monitor a patient's blood oxygen level. Currently, hospitals routinely monitor blood oxygenation by pulse oximetry with a monitor attached to the patient's finger or earlobe as described for example in Silva et al., "Near-infrared transmittance pulse oximetry with laser diodes", J. Biomed. Opt. 8(3), 525-533 (2003). Typically the oxygen monitor is a pair of light-emitting diodes (LED) and photodiodes on a probe clipped to a part of the patient's body. Red light from the LED reflects from the blood in a part of the patient's body, such as an ear-lobe or finger-tip. As a patient's oxygenation level drops, the blood becomes more blue, reflecting less red light to the photodiode. Such blood-oxygen monitors customarily measure percent of normal. Reassuring (normal) ranges are from 95 to 100 percent. For a patient breathing room air, at not far above sea level, an estimate of arterial oxygenation can be made from the blood-oxygen monitor reading. Unfortunately, measurements from such oxygen monitors cannot be reliably correlated to oxygenation in the patient's venous blood. Venous oxygen saturation is also a valuable parameter in the diagnosis of septic and cardiogenic shock as described below.

Other methods of measuring oxygenation: Diffuse optical tomography methods as described for example in Boas et al., Method for monitoring venous oxygen saturation", US Patent application 20040122300 are conceptually appealing but are useful only where the vessels in the vicinity of the diffusing photon field are isolated veins. The presence of mixed arterial and venous blood complicates the problem to as described by Wolf et al., "Continuous noninvasive measurement of cerebral arterial and venous oxygen saturation at the bedside in mechanically ventilated neonates", Crit. Care. Med 25(9), 1579-1582 (1997).

Ultrasound-tagged optical spectroscopy involves overlapping an ultrasound wave and a diffusing optical field, and modulating the frequency of the probe photons or their trajectories. A number of different technologies have been developed that utilize some interaction between ultrasound radiation and electromagnetic radiation. U.S. Pat. No. 5,212,667 to Tomlinson et al. and U.S. Pat. No. 5,174,298 to Dolfi et al. teach the technique of ultrasound tagged frequency-modulated imaging. Other patents teaching variations on the theme of frequency-modulated ultrasound tagging techniques include U.S. Pat. No. 6,815,694 to Sfez et al., U.S. Pat. No.

6,738,653 to Sfez et al., U.S. Pat. No. 6,041,248, to Wang, U.S. Pat. No. 6,002,958 to Godik, U.S. Pat. No. 5,951,481 to Evans, U.S. Pat. No. 5,293,873 to Fang. Trajectory modulation is detected by monitoring the speckle pattern of the photons emerging form the target. Image reconstruction techniques are then used to recreate a map of the path the photons followed in the medium. Imaging the speckle resulting from trajectory changes requires significant computation power and post-processing to yield an image. The technique has limited resolution, and is not yet capable of yielding functional (oxygenation) information in a fast flowing vessel.

Some variations of ultrasound-tagged frequency-modulated imaging rely on observing the frequency shift induced by the photoacoustic effect when an electromagnetic wave interacts in a medium with a sound wave. The electromagnetic wave (having a characteristic frequency $\omega_{OPT}$) receives a frequency shift at the ultrasound frequency $\omega_{US}$ to either the + or − side of the carrier wave $\omega_{OPT}$. Frequency modulation is detected by measuring the frequency shifted photons by for example using a Fabry-Perot etalon as described by Sakadzic and Wang, "High resolution ultrasound modulated optical tomography in biological tissues", Opt. Lett. 29(23) 2004, p 2770-2772. Since the Doppler shifts induced by the ultrasound wave are very small compared to the probe photon carrier wave frequency, the detection system must be extremely sensitive to small frequency shifts. In addition, the frequency shift can be to both larger and smaller frequency of the initial carrier wave, and therefore some self-cancellation may result.

SUMMARY OF THE INVENTION

There is a need in the art to be able to measure venous oxygen saturation levels in various vascular structures in the body, and from this be able to calculate cardiac output. There is a need to make these measurements non-invasively or with minimal invasiveness. There is a need to be able to make these measurements in an MRI-/CT/X-Ray instrument compatible manner, thus preferably not using ferromagnetic materials in construction, and using designs such that the probe on/in the body may be remotely coupled to the control system away from the magnetic field or ionizing radiation sources generated by the MRI instrument or CT/X-Ray. There is a need in the art to make these measurements in a manner that does not depend on the melanin content of the skin. There is a need to make these measurements in a manner such that the result may be arrived at in a short time period, i.e. such that extensive post-processing of the data is not required, so that the physician may make accurate timely diagnostic and therapeutic decisions. Many or all of the disadvantages associated with the prior art can be significantly alleviated through embodiments of the present invention.

According to certain embodiments of the present invention a system for monitoring one or more parameters relating to blood, such as oxygenation, pH or cardiac output, is provided including optical transmitters configured to generate radiation containing photons having a specific interaction with at least one target chromophore in a target structure, preferably a blood vessel such as the interior jugular vein. The optical transmitters are adapted and positioned to transmit the radiation from the optical transmitter into at least a first area including a substantial portion of the target structure and into a second area not including a substantial portion of the target structure. Optical receivers are configured and positioned to detect a portion radiation scattered from at least the first area and the second area. A processor is adapted to estimate the one or more parameters relating to the patient's blood, the estimation being based in part on the scattered radiation detected from the first area, and the scattered radiation from the second area. A processor preferably estimates average tissue scattering and absorption properties for the radiation associated with the second area, and calculates a probability for the radiation to pass through the first area and the second area using a photon diffusion equation. Estimates or calculations are thereby made by relating probabilities for the radiation to pass through the first and second areas. Radiation may also be transmitted into a third area including a substantial portion of a second target structure, such as the carotid artery. The launch optics and collecting optics are preferably mounted on a sensor patch designed to be engaged to the patient's skin.

The system can also include a portable unit which houses the optical source, detectors, processor and wireless communications. The portable unit can be sized such the patient can carry the portable unit for extended periods.

An ultrasound transducer can also be used in combination with the optical methods generate an image of tissues within the first area including the target structure to enable placement of the one or more optical transmitters and the one more optical receivers on the patient so as to enhance the accuracy of the monitoring of the system. The ultrasound transducer can also be configured to provide an ultrasound radiation pressure field to modulate the target structure at a modulation frequency. The ultrasound pressure modulation can be preformed continuously, or it can be operated temporarily, in order to calculate a calibration adjustment to the optical measurement.

The present invention is also embodied in a pad of pliable material adapted to be engaged on the skin of a patient. Launch optics can be mounted on the pad and positioned so as to enable transmission of photons generated by an optical source through the patient's skin into at least a first area including a substantial portion of a target blood vessel and into a second area not including a substantial portion of the target blood vessel. Collecting optics can be mounted on the pad and positioned to so as to enable detection of the photons having been scattered within the first area and the second area.

The present invention is also embodied in a method for monitoring one or more parameters relating to blood of a patient. Optical transmitters and receivers are engaged on a tissue boundary, such as skin, of the patient. Radiation is generated containing photons having a specific interaction with a target chromophore in a target structure within the patient. The radiation is transmitted through the optical transmitters into a first area including a substantial portion of the target blood vessel and into a second area not including a substantial portion of the target structure. Optical receivers detect a portion of the radiation scattered from at least the first area and the second area. The parameter(s) relating to a patient's blood can be estimated based in part on the detected scattered radiation from the first area, and the scattered radiation from the second area.

BRIEF DESCRIPTION OF THE DRAWINGS

The teachings of the present invention can be readily understood by considering the following detailed description in conjunction with the accompanying drawings, in which:

FIGS. 12A-12B are schematic diagrams of sensors that can be used with embodiments of the present invention.

FIG. 12C is a three-dimensional diagram of an alternative sensor according to an embodiment of the present invention.

FIG. 12D is a cross-sectional diagram taken along line D-D of FIG. 12C.

FIG. 18A is sagittal cross-sectional schematic diagram illustrating a normal heart.

FIG. 18B is a sagittal cross-sectional schematic diagram illustrating a heart exhibiting Patent Ductus Arteriosus (PDA).

FIG. 18C is a sagittal cross-sectional schematic diagram illustrating a heart exhibiting Patent Foramen Ovale (PFO).

FIG. 19 is a thoracic axial cross-sectional schematic diagram illustrating examples of sensor placement for cardiac mapping in newborn infants according to an embodiment of the invention.

DESCRIPTION OF THE SPECIFIC EMBODIMENTS

Figure 1:
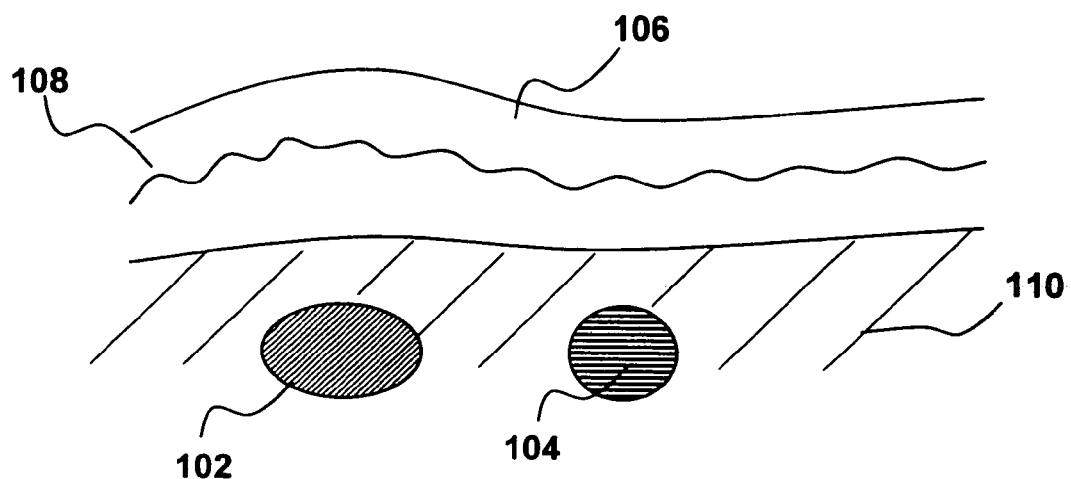
FIG. 1 is a schematic view of an embedded vascular structure that is an example of a suitable target for measurement with embodiments of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

GLOSSARY

As used herein, the following terms have the following meanings:

Continuous wave (CW) laser: A laser that emits radiation continuously rather than in short bursts, as in a pulsed laser.

Diode Laser: Refers to a light-emitting diode designed to use stimulated emission to generate a coherent light output.

Diode lasers are also known as laser diodes or semiconductor lasers. A diode-pumped laser refers to a laser having a gain medium that is pumped by a diode laser.

Mode locked laser: A laser that emits radiation in short bursts, as in a pulsed laser. Typically these pulses are on the order of 0.1-100 picoseconds in temporal length and preferably 1-50 picoseconds.

Highly Non-linear Fiber: A fiber characterized by having a guiding core with properties that can be used to convert electromagnetic radiation at one frequency to another provided there is sufficient intensity at the originating frequency and the fiber has sufficient length.

Upconversion Process: A process by which photons of a given frequency are converted to photons of shorter wavelength (higher frequency). This technique may be used, e.g., to bring infra-red photons into the detection range of silicon detectors for example, or may be used in a pulsed configuration to give temporal selectivity in which photons are upconverted and hence detected.

Non-Linear Crystal: A crystal made of a material having special optical properties allowing the frequency of an incoming electromagnetic wave to be shifted according to predictable rules and conditions.

Optical Parametric Oscillator: A process by which a photon at a pump frequency $\omega_p$ is converted in a material inside a resonator to two photons of lower frequency, typically called the signal and idler photons with the relationship:

$$\omega_P = \omega_{SIG} + \omega_{IDL}$$

Optical Parametric Amplifier: A process by which a photon at a pump frequency $\omega_p$ is converted in a material (but without the need for an external resonator) to two photons of lower frequency, typically called the signal and idler photons with the relationship:

$$\omega_p = \omega_{sig} + \omega_{idl}$$

As stated above, there are eight desirable characteristics for cardiac output (CO) monitoring techniques: accuracy, reproducibility or precision, fast response time, operator independency, ease of use, continuous use, cost effectiveness, and no increased mortality and morbidity associated with its use. None of the present CO monitoring techniques satisfactorily combines all eight criteria mentioned above.

The Fick principle involves measuring the oxygen consumption ($VO_2$) per minute (e.g., using a spirometer), measuring the oxygen saturation of arterial blood using for example standard pulse oximetry on the finger, and measuring venous oxygen saturation in the pulmonary artery or superior vena cava.

From these values, one can calculate:

$$\text{Cardiac Output} = \frac{\text{Oxygen\_Consumption}}{(\text{ArterialSaO}_2 - \text{VenousSaO}_2) \times [Hb] \times 1.36}$$

where Arterial $SaO_2$ and Venous $SaO_2$ are respectively the arterial and venous oxygen saturation, [Hb] is the blood hemoglobin concentration and 1.36 is a factor subsuming the oxygen carrying capacity of the hemoglobin. [Hb] can be related simply to the hematocrit (Hct), a routinely measured parameter defined as the percent of whole blood that is composed of red blood cells (erythrocyte volume to total volume expressed as a percentage). The range for Hct is 32-50% in "normal" "healthy" people. Hct does not tend to change dramatically and quickly (unless the patient is bleeding severely), so it is sufficient to take a sample every 4-6-8 hours for example and update the Fick calculation periodically. Hematocrit (hct) can be measured, e.g., by taking a sample of blood and spinning it down in a centrifuge and calculating the volumes.

The Fick principle relies on the observation that the total uptake of (or release of) a substance by the peripheral tissues is equal to the product of the blood flow to the peripheral tissues and the arterial-venous concentration difference (gradient) of the substance. In the determination of cardiac output, the substance most commonly measured is the oxygen content of blood, and the venous saturation is measured in the pulmonary artery using a catheter as for example described by Powelson et al., "Continuous monitoring of mixed venous oxygen saturation during aortic operations", Crit. Care Med. 20(3), 332-336 (1992). This gives a simple way to calculate the cardiac output. The drawback of drift associated with this type of catheter has been discussed by Souter et al., "Jugular venous desaturation following cardiac surgery", Brit. J. Anaesth. 81, 239-241 (1998). It is also highly invasive, incompatible with ambulatory measurement, and poses risks of infection due to vascular system breach (femoral or jugular vessel insertion). The nature of the challenge is illustrated schematically in FIG. 1. An embedded vascular structure of a body 100 includes an artery 102 and vein 104, for example the internal jugular vein and artery in the neck. The vein 102 and artery 104 are located beneath the epidermis 106 and dermis 108 of the body 100. The vein and artery are embedded in and around subcutaneous structures 110, e.g., fat, muscle, tendon, etc.

Assuming there are no shunts across the cardiac or pulmonary system, the pulmonary blood flow equals the systemic blood flow. Measurement of the arterial and venous oxygen content of blood involves the sampling of blood from the pulmonary artery (low oxygen content) and from the pulmonary vein (high oxygen content). In practice, sampling of peripheral arterial blood is a surrogate for pulmonary venous blood.

Embodiments of the present invention allow non-invasive or minimally invasive measurement of venous oxygen saturation at a point where the value trends correctly with a direct pulmonary artery catheter measurement. One can apply the above-described Fick principle to such a measurement thereby enabling measurement of cardiac output in a non- or minimally invasive manner. Embodiments of the present invention for measuring venous oxygen saturation can also be made insensitive to the presence of shunts in the heart, such as for example acquired ventricular septal defects, and as such offer valuable adjunct information if PAC thermodilution or Fick data are already available. This is the case when the sensor is placed on the internal jugular vein.

The value of the venous oxygen saturation is also a useful adjunct diagnostic parameter in its own right. Patients with low cardiac output tend to have low venous oxygen saturation, for example around 50. This low value results from the increased extraction of oxygen in the body tissues due to the poor perfusion resulting from low flow. However high mixed venous oxygen saturation with low cardiac output can indicate a significant left-to-right shunt across the heart, such as an acquired ventricular septal defect. Embodiments of the present invention where the sensor is placed on the internal jugular will allow a measurement of venous oxygen saturation before the heart and pulmonary system, and thus will in insensitive to the presence of these shunts.

Also by way of example a presentation of high cardiac output, high venous oxygen saturation, narrow arteriovenous difference and low peripheral resistance might suggest to the physician to test for septic shock. On the other hand cardiogenic shock is associated with high peripheral resistance. Thus measurement of cardiac output can help guide and monitor the administration of drugs such as vasodilators/vasoconstrictors and inotropes.

A number of different technologies have been developed that utilize some interaction between ultrasound radiation and electromagnetic radiation. However, these prior art technologies are all distinguishable from the techniques described herein. For example, embodiments of the present invention are superior to standard ultrasound-tagged photon techniques in that they are not limited by the ability of the apparatus to detect very small frequency shifts on the detected photons. U.S. Pat. No. 5,212,667 to Tomlinson et al. and U.S. Pat. No. 5,174,298 to Dolfi et al. teach the technique of ultrasound tagged frequency-modulated imaging. Other patents teaching variations on the theme of frequency-modulated ultrasound tagging techniques include U.S. Pat. No. 6,815,694 to Sfez et al., U.S. Pat. No. 6,738,653 to Sfez et al., U.S. Pat. No. 6,041,248, to Wang, U.S. Pat. No. 6,002,958 to Godik, U.S. Pat. No. 5,951,481 to Evans, U.S. Pat. No. 5,293,873 to Fang.

Ultrasound-tagged frequency modulated imaging relies on observing the frequency shift induced by the photoacoustic effect when an electromagnetic wave interacts in a medium with a sound wave. The electromagnetic wave (having a characteristic frequency $\omega_{OPT}$) receives a frequency shift at the ultrasound frequency $\omega_{US}$ to either the + or − side of the carrier wave $\omega_{OPT}$. Heterodyne or interferometric techniques are then used to decouple the frequency shifted wave from the carrier wave. Implementation of the technique requires sophisticated lasers with narrow linewidths and concomitantly long coherence lengths in order to resolve the two frequencies. U.S. Pat. No. 6,002,958 to Godik teaches the study of the amplitude modulation induced on an electromagnetic wave by the ultrasound beam and scanning the ultrasound beam in order to form an image of the absorber.

U.S. Pat. No. 6,264,610 to Zhu teaches the use of ultrasound and near-IR imaging as adjunctive imaging techniques, but does not attempt a physical link between the two techniques.

U.S. Pat. No. 5,452,716 to Clift teaches the use of two-wavelength probing using one wavelength specific to the substance being probed and a reference field characterized by another wavelength. This patent does not teach any form of temporal gating, any form of targeting a structure, or any form of depth control using co-located optical and ultrasound fields.

U.S. Pat. No. 6,445,491 to Sucha et al. and U.S. Pat. No. 5,936,739 to Cameron et al. teach the use of optical parametric processes to amplify signals in imaging systems. Neither of these patents teaches the use of upconversion to produce a signal which is necessarily free from background contamination from for example fluorescence processes or Raman scattering. Neither of the patents teaches the use of the very fast non-linearities found in fiber Optical Parametric Amplifiers to yield time-gated information in a straightforward manner.

U.S. Pat. No. 5,451,785 to Faris teaches the use of upconversion processes in a transillumination imaging system.

U.S. Pat. No. 6,665,557 to Alfano et al. teaches spectroscopic and time-resolved optical methods for imaging tumors in turbid media where time gating of the ballistic and near-ballistic photons is used to improve the reconstruction of the image. The more diffusely scattered photons are rejected in this technique and no attempt is made to localize the interaction using ultrasound.

U.S. Patent Appl. No. 2004/0122300 A1 Boas et al., U.S. Patent Appl. No. 2004/0116789 to Boas et al., U.S. Pat. No. 6,332,093 to Painchaud et al., U.S. Pat. No. 5,630,423 to Wang et al., U.S. Pat. No. 5,424,843 to Tromberg et al. and U.S. Pat. No. 5,293,873 to Fang teach variations on the theme of Photon Migration Spectroscopy, Photon Migration Imaging (PMI), Diffuse Optical Tomography (DOT), or Diffuse Imaging, where photons from a source diffuse through the target and are detected using detectors placed at various distances from the source launch point. The characteristics of the diffusing photons are interpreted to yield functional and structural information about the medium they have diffused through. No attempt is made to "tag" these photons to localize the region of interaction. No attempt is made to time-gate the detected signal. Embodiments of the present invention are superior to Photon Migration Imaging (PMI, DOT etc) in that they allow accurate depth and location localization of the target.

Embodiments of the present invention are also superior to speckle based imaging techniques because they are insensitive to the speckle decorrelation time of the tissue being probed. This speckle decorrelation is very fast in larger vascular structures with flowing blood inside, preventing use of speckle-based techniques in the types of vessels the current invention aims to address.

Embodiments of the present invention can also be designed in such a way as to be insensitive to the presence of epidermal melanin (unlike many of the wavelengths used in PMI/DOT and ultrasound tagged spectroscopy and imaging). Embodiments of the present invention can also be designed in a manner that will not suffer from significant solar or environmental background light contamination.

Embodiments of the present invention do not require the development of sophisticated single frequency lasers and interferometric detection techniques. As a result embodiments of the present invention will be simpler to implement and more technologically robust in a clinical setting. Apparatus according to embodiments of the present invention can use proven telecommunication-based fiber-based technology to yield a robust, small, and efficient product.

Embodiments of the present invention do not require 2-D imaging arrays or cameras (for example CCD cameras), and in particular do not require infra-red detector arrays such as InGaAs CCDs. These devices need to be cooled to achieve low noise conditions, further complicating the experimental/clinical implementation. Apparatus according to embodiments of the present invention can use proven single element silicon detectors which do not need to be cooled and which do not need extensive computational support.

Figure 2A:
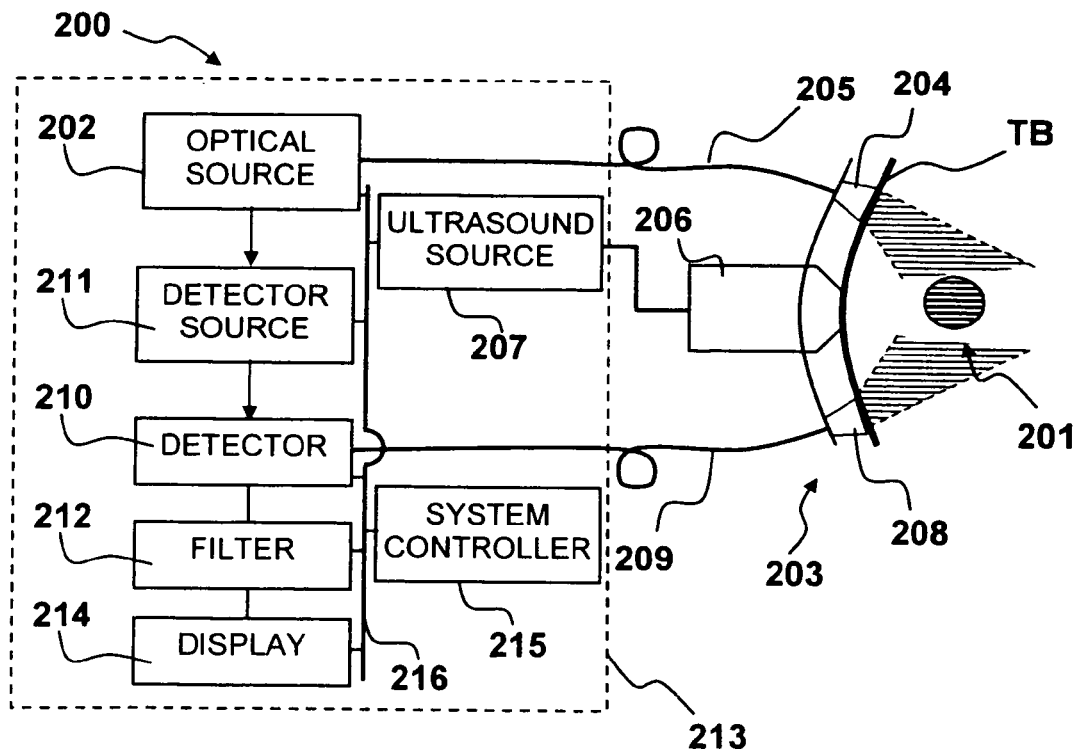
FIG. 2A is a schematic diagram of an apparatus according to an embodiment of the present invention.

FIG. 2A is a schematic block diagram of a diagnostic apparatus 200 according to an embodiment of the present invention. The apparatus 200 generally includes an optical source 202, launch optics 204, an ultrasound transducer 206, collection optics 208, an optical detector 210, associated electronics such as a filter 212 and an optional display 214. The optical source 202 provides pulsed electromagnetic radiation. The launch optics 204 may include one or more optical fibers 205 that couple the electromagnetic radiation from the optical source 202 to a body 201. Similarly the collecting optics 208 collect optical signals reflected from within the body 201. The collecting optics 208 may also include one or more optical fibers 209 that couple signals scattered electromagnetic radiation to the optical detector 210. The optical source 202 may supply a timing signal (which may be either optical or electronic) to trigger a detector source 211 that provides an optical signal used in detection of the scattered radiation.

In some embodiments the launch optics 205, ultrasound transducer 206, and collecting optics may be mounted together in a handpiece to form a combined ultrasound optical sensor 203. In other embodiments, the detector 210 may be part of the sensor 203 without the need for collecting optics. In some embodiments, the optical source 202, optical detector 210, detector source 211, filter 212, display 214 and an ultrasound generator 207 may be part of a remote unit 213 coupled to the sensor 203 by fiberoptics 205, 209 and electrical cables. The remote unit 213 may include a system controller 215. The system controller 215 may include a central processor unit (CPU) and a memory (e.g., RAM, DRAM, ROM, and the like). The controller 215 may also include well-known support circuits, such as input/output (I/O) circuits, power supplies (P/S), a clock (CLK), Field Programmable Gate Arrays (FPGAs) and cache. The controller 215 may optionally include a mass storage device such as a disk drive, CD-ROM drive, tape drive, or the like to store programs and/or data. The controller may also optionally include a user interface unit to facilitate interaction between the controller 215 and a user. The user interface may include a keyboard, mouse, joystick, light pen or other device. The preceding components may exchange signals with each other via a controller bus. In addition, the optical source 210, detector source 211, filter 212, display 214 and an ultrasound generator 207 may exchange signals with the controller 215 via the system bus 216.

The controller 215 typically operates the optical source, 202, ultrasound generator 207, optical detector 210, detector source 211 detector, filter 212 and display 214 through the I/O circuits in response to data and program code instructions stored and retrieved by the memory and executed by the processor. The program code instructions may implement embodiments of the diagnostic technique described herein. The code may conform to any one of a number of different programming languages such as Assembly, C++, JAVA, Embedded Linux, or a number of other languages. The CPU forms a general-purpose computer that becomes a specific purpose computer when executing program code. Although the program code is described herein as being implemented in software and executed upon a general purpose computer, those skilled in the art will realize that the method of pulsed pumping could alternatively be implemented using hardware such as an application specific integrated circuit (ASIC) or FPGA or other hardware circuitry. As such, it should be understood that embodiments of the invention can be implemented, in whole or in part, in software, hardware or some combination of both.

Figure 2B:
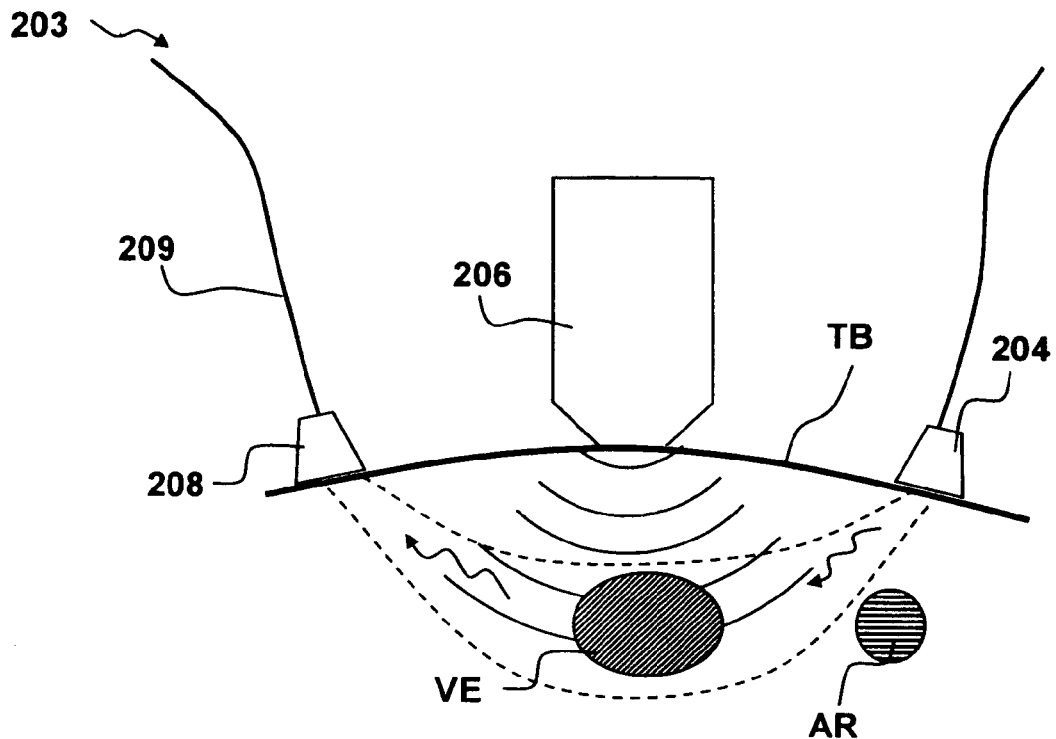
FIG. 2B is a close-up cross-sectional schematic diagram illustrating an example of use of the apparatus of FIG. 2A

Operation of the apparatus 200 may be understood with respect to the close-up schematic diagram depicted in FIG. 2B. An embedded target structure within the body 201 such as an artery AR or vein VE can be identified by ultrasound imaging.

The ultrasound generator 207 and transducer 206 can be used to do both the ultrasound imaging and the target modulation. Once a target has been located, the apparatus 200 switches between a regular ultrasound mode (imaging) and a radiation pressure modulation mode, firing tone bursts to modulate the target. The basic approach is first to image to choose a location to deliver radiation pressure and then to apply the appropriate phase to the array elements of the transducer 206 to have a focus at the location of interest. The radiation pressure is supplied by applying a tone burst (many cycles of electrical signal at the frequency of operation of the array) from the ultrasound generator 207 to the elements of the array in the transducer 206. The repetition rate at which the tone burst is applied is the frequency at which the radiation pressure is applied. This repetition rate is constrained at the upper end by the fundamental frequency of the ultrasound transducer 206, i.e. the tone burst cannot have a higher repetition rate than the fundamental frequency of the transducer itself. By way of example, the ultrasound transducer 206 can operate at fundamental frequencies in the range 2-50 MHz, and preferably from 2-15 MHz. The tone bursts may produce radiation pressure modulation occurring at frequencies between 50 Hz and 750 kHz.

The sensor 203 is then placed proximate to a tissue boundary TB of the boundary 201. The target structure is then vibrated using radiation pressure from the transducer 206 and illuminated with a diffuse photon field with a characteristic frequency $\omega_{INJ}$ delivered from the optical source 202 via the launch optics 204. The radiation-pressure modulation of the target is detected by its effect on the emerging photon field at the detector (e.g., via the collecting optics 208). In the example depicted in FIGS. 1 and 2A, it may be possible to measure both venous and arterial oxygenation separately by illuminating and modulating the vein and then separately illuminating and modulating the artery. In the case where the target is the internal jugular vein, the corresponding arterial structure is the carotid artery. This method, when it can be used, will implicitly provide a calibration signal. Cardiac output can then be calculated from the Fick Principle, as described above.

To make the measurement a biological structure within the body 201, such as the pulmonary artery, descending branch of the aorta, internal jugular, or external jugular, is located in a standard manner with medical imaging. Once found the combined ultrasound/optical sensor 203 can be positioned proximate to the targeted structure. This can either be external dermal placement, e.g., on the neck in the case of the internal jugular vein, or an inserted catheter, either endotracheally for direct access to the left pulmonary artery and thoracic aorta, or trans-esophageally for access to the right pulmonary artery. The sensor 203 is preferably positioned such that the distance between the emitting tip of the launch optics 204 and the lumen of the targeted vessel is approximately minimized.

The ultrasound transducer 206 is used to physically modulate (vibrate) the selected target using ultrasound radiation pressure. The ultrasound transducer 206 is designed to focus its acoustic output into the target at various modulation frequencies. Examples of ultrasound transceivers that can provide such focused output include phased array ultrasound transceivers and single element ultrasound transducers with imaging designs. Phased array transducers typically have an array of ultrasound transducer elements that are narrow and have a wide acceptance angle so that energy from various angles is collected, and so that several elements (if not all) in the array contribute to the focusing at a certain location. To generate a beam, the various transducer elements are pulsed at slightly different times. By precisely controlling the delays between the transducer elements, beams of various angles, focal distance, and focal spot size can be produced. Furthermore, for a given point within the targeted tissue a unique set of delays will maximize the constructive interference of acoustic signals from each of the transducer elements. Such transducers can therefore selectively modulate particular structures within the target without modulating surrounding structures. Beam forming in ultrasound refers to the signal processing scheme used to focus the signals from various transducers. The energy is preferentially deposited using focusing to allow the application of radiation pressure at the location of interest with a relatively low level of input signal.

Examples of suitable ultrasound transducers include, for example, the GE Logiq 7 BT03 made by General Electric of Fairfield, Conn., or the Aspen® Echocardiography System made by Siemens (Acuson) of Mountain View, Calif. Other suitable array transducers are made by Philips (The Netherlands), or Hitachi (Japan). It is best to choose an instrument that is used commonly in hospitals say to image the heart.

An ultrasound imaging system can also be used in association with the ultrasound generator 207 and transducer 206 to locate the blood vessels in order to orient the delivery of the pulsed radiation from the optical source 202. The imaging system can be incorporated into the system controller 215. The transducer 206 can be a piezo type transducer as used in the above-described commercially-available ultrasound machines or a cMUT (capacitative Micromachined Ultrasonic Transducer), see X. Jin, I. Ladabaum, B. T. Khuri-Yakub. "The Microfabrication of Capacitive Ultrasonic Transducers", J. Microelectromechanical Systems vol. 7, pp. 295-302, September 1998. and U.S. Pat. No. 6,262,946 to Khuri-Yakub et al, both of which are incorporated herein by reference. Using the cMUT will allow a very compact 2-D array to be made. Such compact arrays are very important for ring-shaped transducers such as that shown in FIGS. 12C-12D for the trans-tracheal/trans-esophageal applications.

Using an array or other beam-forming transducer one can steer the ultrasound from artery to vein using phase, and alternately modulate each one, allowing a direct calibration of the optical signal. For example one can steer the beam from internal jugular to carotid artery, alternatively sampling 100% oxygen saturated blood and the venous blood with reduced saturation. The ultrasound imaging system can also be used to derive the width of the arteries and veins, and the blood flow velocity using Doppler shift of the scattered ultrasound. Such a measurement can provide an estimate of the cardiac output that can be compared to cardiac output as derived from the use of the apparatus 200. This adjunct measurement will have additional diagnostic value as discussed above for the diagnosis of shunts, septic and cardiogenic shock etc.

Once the ultrasound transducer 206 and launch optics 204 are aligned with respect to the targeted vessels, the array of transducers in the ultrasound imaging system will all be fired, with appropriate phase delays, with a burst of energy to deliver radiation pressure at the focus as determined by the phase delays. The focus of the acoustic signal can be chosen to be inside the vessel acting on the blood cells, or on the side walls of arteries. The radiation pressure associated with the acoustic pulse which is equal to the acoustic intensity divided by the speed of sound in the medium, will act to impart a movement on the cells or arterial walls on which it acts. The use of radiation pressure (alternatively "radiation force") to induce motion in a target which is then detected by conventional ultrasound techniques has been described by Nightingale et al "Acoustic Radiation Force Impulse Imaging: In Vivo Demonstration of Clinical Feasibility", *Ultrasound in Medicine and Biology*, 28(2): 227-235, (2002) and in U.S. Pat. No. 6,371,912 to Nightingale et al, both of which are incorporated herein by reference. Embodiments of the present invention are superior to this technique in that they will permit functional (oxygenation) information to be derived from the target, whereas in the aforementioned prior art only mechanical information (stiffness, elasticity etc) is derived.

In this fashion, the optical signal, which relates to the oxygen content in the blood cells in the target volume, will be modulated at the frequency at which the radiation pressure pulse is applied, $\omega_{RPM}$. For instance, using a 7.5 MHz imaging system, one can use a burst of say 10 cycles at any repetition rate up to around 750 kHz as determined by the physical and mechanical properties of the target and the experimental implementation. It may be possible to tune the interpulse spacing (the repetition rate) in the tone burst to resonantly modulate the target depending on its elastic properties. It may also be possible to tune the ultrasound fundamental frequency to optimize its interaction with the desired target (blood cells, vessel walls etc). In this manner the detector 210 may detect only those photons which have interacted with the desired target 201.

The optical source 202 may be configured to deliver the temporally correlated groups of photons at a repetition rate of between about 100 kHz and about 500 MHz, preferably between about 1 MHz and about 250 MHZ, more preferably between about 10 MHz and about 200 MHz. The groups of photons may be in the form of pulses having pulse widths in the range of about 1 picosecond to about 1 nanosecond, preferably, about 1 to 100 picoseconds, more preferably about 5 to 50 picoseconds. The photons may be characterized by wavelengths between about 650 nm and about 1175 nm, preferably between about 650 nm and about 930 nm or between about 1020 nm and about 1150 nm.

The optical source 202 provides temporally correlated photons at two or more different wavelengths. For example radiation from a pulsed laser may be incident on a device that converts radiation at the fundamental frequency of the laser into a pair of photons at two different predetermined frequencies. Such a device could be a nonlinear crystal causing Spontaneous Parametric Down Conversion (SPDC) as for example described by Shi and Tomita, "Highly efficient generation of pulsed photon pairs with bulk periodically poled potassium titanyl phosphate", J. Opt. Soc. Am. B. 21(12) 2081-2084 (2004), or a highly non-linear fiber source as described by Rarity et al., "Photonic crystal fiber source of correlated photon pairs", Opt. Exp. 13(2), 534-544 (2005).

Alternatively the optical source 202 may include a nonlinear crystal phased matched to act as an optical parametric oscillator (OPO) to provide a temporally correlated photon pair. An OPO takes a fundamental electromagnetic wave at frequency $\omega_{P1}$ and converts it to two new frequencies called the signal and idler, $\omega_{SIG}$ and $\omega_{IDL}$ related by the equation $$\omega_{P1} = \omega_{sig} + \omega_{idl}$$

where the signal and idler waves are emitted in temporal coincidence.

The OPO may be driven by the second harmonic of a pulsed laser operating at a fundamental frequency $\omega_{P1}$ to create two new frequencies called the signal and idler, $\omega_{SIG}$ and $\omega_{IDL}$ related by the equation $$2\omega_{P1} = \omega_{sig} + \omega_{idl}$$

where $2\omega_{P1}$ is the second harmonic of the fundamental frequency. For example the drive laser may be a mode-locked or Q-switched Nd:YAG laser operating at 1064 nm, giving a second harmonic wave at 532 nm. This wave in turn is used to drive the OPO. In this manner three clinically useful, temporally coincident photon waves at 1064 ($\omega_{P1}$), 1030 ($\omega_{sig}$) and 1100 ($\omega_{idl}$) may be generated. The nonlinear crystal may be selected from a variety of substances, for example BBO, LBO, KTP, KTA, RTP, or periodically poled materials such as periodically poled lithium Niobate (PPLN), periodically poled stoichiometric lithium tantalate (PP-SLT) and the like. Such materials are described, e.g., in the freeware program SNLO distributed by Sandia National Laboratories, Albuquerque, N. Mex.

By way of example, the optical source 202 may include a pulsed solid state laser, for example a picosecond mode-locked laser such as the picoTRAIN™ series compact, all-diode-pumped, solid state picosecond oscillator manufactured by High-Q Lasers of Kaiser-Franz-Josef-Str. 61 A-6845 Hohenems Austria. The source may also be a mode-locked fiber laser, such as the picosecond version of the Femtolite™ D-200 from IMRA America Inc., Ann Arbor Mich. 48105. Alternatively, a picosecond pulsed diode such as the PicoTA amplified picosecond pulsed laser diode heads manufactured by Picoquant, of Berlin, Germany, may be used as the optical source 202. The optical fibers 205 coupling the optical source 202 to the launch optics 204 may be, e.g., single mode fiber optic, such as the P1-980A-FC-2—Single Mode Fiber Patch Cable, 2m, FC/PC manufactured by Thorlabs, Inc. of Newton, N.J. Radiation coupled from the optical source 202 to the target 201 via the launch optics 204 is used, e.g., to illuminate the lumen of a selected blood vessel with pulses of radiation at two or more different wavelengths carefully chosen to have deep penetration into tissue, to have differing affinities for oxy- and deoxy-hemoglobin, or for oxy-hemoglobin and met-hemoglobin, but to have substantially similar scattering cross-sections and anisotropy parameters.

Some of the radiation scatters from the target 201 and is collected by the collecting optics 208 and/or detector 210. By detecting pairs or multiplets of photons at different wavelengths returning from the target tissue in substantial temporal coincidence, it can be inferred that the coincident photons have traveled approximately the same path length in the tissue. This is the main difference between making measurements in clear transparent media where the Beer-Lambert law may be presumed to apply, and making measurements in turbid media where elastic scattering causes a substantial and generally indeterminate pathlength increase, as discussed by Okui and Okada, "Wavelength dependence of cross-talk in dual-wavelength measurement of oxy- and deoxy-hemoglobin", J. Biomed. Opt. 19(1), 011015 (2005).

The detector is coupled to a filter 212 that selects coincident photon signals having modulation at the radiation pressure modulation frequency or a harmonic thereof. The filter 212 may be coupled to the display 214, e.g. a CRT screen, flat panel screen, computer monitor, or the like, that displays the results of the aforementioned process in a manner readily interpretable, e.g., in the form of text, numerals, graphical symbols or images.

By detecting arrival rates of pairs or multiplets of photons at the frequency of the radiation pressure modulation or a harmonic of the radiation pressure modulation frequency, one can infer that these photons interacted with the radiation-pressure-modulated target 201. If the target 201 contains the oxygenated or deoxygenated forms of hemoglobin (Hb), the detected pair or multiplet coincidence rate will be altered depending on how the wavelengths were selected. The extent to which the detection rate is altered can be correlated to the oxygenation level of the target or to the pH in the target. The met-hemoglobin absorption spectrum is dependent on pH as shown in Zijlstra et al., "Visible and Near Infrared Absorption Spectra of Human and Animal Haemoglobin, 1$^{st}$ ed. Utrecht: VSP Publishing; 2000, page 62. Thus a non-invasive probe of met-Hb absorption may be used to probe the pH of the structure being targeted.

Figure 3:
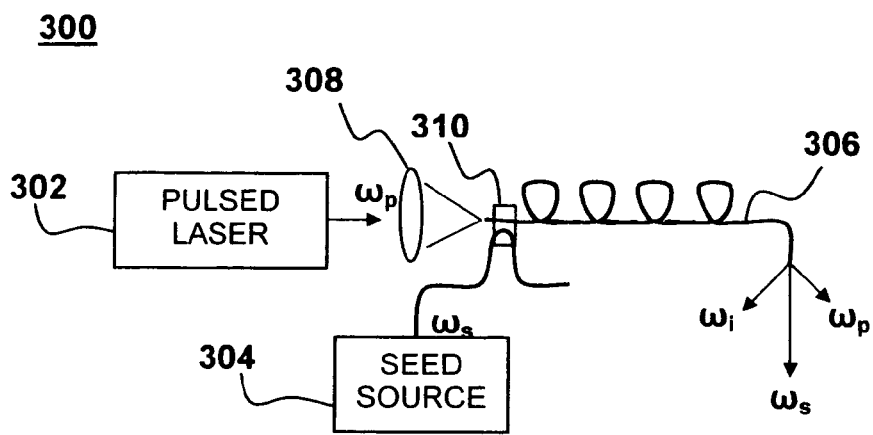
FIG. 3 is a schematic diagram of a three-wavelength pulsed optical source for use in embodiments of the present invention.

There are many possible configurations for the optical source 202 of FIG. 2A. For example, FIG. 3 is a schematic diagram of a three-wavelength pulsed optical source 300 that emits three laser pulses at the three wavelengths with temporal coincidence. This could be the OPO source described above. Alternatively the source 300 generally includes a pulsed laser 302, a seed source 304, and a highly non-linear fiber (HNLF) 306. Optics, 308 such as one or more lenses couple pump radiation at a drive frequency $\omega_p$ to the HNLF 306. A 2×2 coupler 310 couples seed radiation at a frequency $\omega_s$ from the seed source 304 into the HNLF 306. When $\omega_p$ and $\omega_s$ are properly chosen, the HNLF 306 acts as an optical parametric amplifier (OPA) that produces three temporally correlated electromagnetic waves at three frequencies: pump radiation at $\omega_p$, amplified seed radiation at $\omega_s$ and idler radiation at an idler frequency $\omega_{idl}$ given by:

$$\omega_{idl} = 2\omega_p - \omega_s.$$

For example, if $\omega_p$ corresponds to a vacuum wavelength of 1064 nm and $\omega_s$ corresponds to a vacuum wavelength of 1100 nm, $\omega_{idl}$ corresponds to a vacuum wavelength of about 1030 nm.

The fiber 306 preferably has a non-linearity that is high enough to allow non-linear optical effects to occur efficiently in a reasonable length of fiber, and where the non-linearity is sufficiently fast to create the required temporal synchronization between the pump, seed and idler waves. Such fibers may be obtained from Crystal Fibre of Birkenrød, Denmark, for example the NL-5.0-1065 type. The non-linear optics underlying the conversion have been described by for example, Ho et al., "Narrow-linewidth idler generation in fiber four-wave mixing and parametric amplification by dithering two pumps in opposition of phase", J. Lightwave. Tech. 20(3), 469-476 (2002), which is incorporated herein by reference. The drive frequency $\omega_P$ may be provided by a high repetition rate mode-locked picosecond laser, such as the picoTRAIN™ series compact, all-diode-pumped, solid state picosecond oscillator manufactured by High-Q lasers of Kaiser-Franz-Josef-Str. 61 A-6845 Hohenems Austria or a mode-locked fiber laser, such as the picosecond version of the Femtolite™ D-200 from IMRA America Inc., Ann Arbor Mich. 48105.

Figure 4:
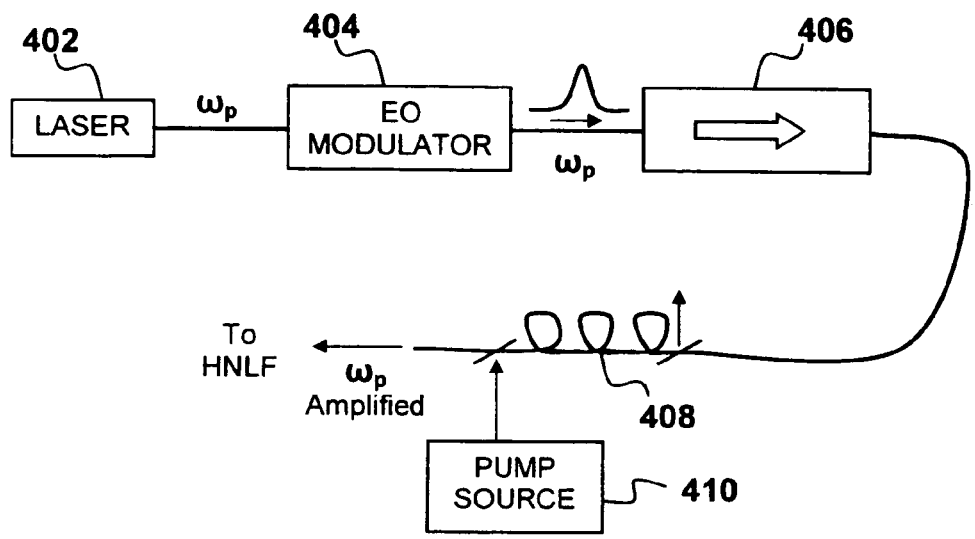
FIG. 4 is a schematic diagram of an all-electronic optical source for use in embodiments of the present invention.

In the source 300 the seed source 304 may be a distributed feedback (DFB) or DBR (Distributed Bragg Reflector) laser, for example the EYP-DBR-1063-00100-2000-SOT02-0000 diode laser manufactured by Eagleyard Photonics, Berlin Germany. There are a number of different possible configurations for the pulsed laser 302. Generally, the pulsed laser 302 should be capable of providing picosecond pulses of pump radiation to the HNLF 306. FIG. 4 is a schematic diagram of an all-electronic optical source 400 of picosecond pulses which could be used as the pulsed laser 302 of FIG. 3. The source 400 generally includes a diode laser 402 an electro-optic modulator (EO) 404 a Faraday isolator 406 and a doped fiber amplifier 408. The diode laser 402 provides radiation at $\omega_p$ which is modulated by the EO modulator 404 to create weak picosecond radiation pulses 401, which are coupled to the fiber amplifier 408. The Faraday isolator 406 transmits pulses to the fiber amplifier 408 and blocks radiation from being reflected back towards the EO modulator. A fiber pump source 410 provides fiber pump radiation (e.g., at a vacuum wavelength of 980 nm) to the cladding or core of the fiber amplifier 408. The fiber amplifier may include a dump for the pump laser so that fiber pump radiation does not oscillate through fiber amplifier 408. The amplifier 408 amplifies the weak pulses 401 to create amplified pulses 403 that can be fed to the HNLF 306.

By way of example, the diode laser 402 is a continuous wave (CW) tunable DFB or DBR diode laser, such as the EYP-DBR-1063-00100-2000-SOT02-0000 diode laser manufactured by Eagleyard Photonics, Berlin Germany The EO modulator 404 may be a Model 4853 6.8/9.2-GHz Modulator from New Focus (Bookham) San Jose, Calif. The Faraday isolator 406 may be a model 4I1055 from Electro-Optic technology, of Traverse City, Miss. The fiber amplifier 408 may be doped with Ytterbium or Neodymium, such as the DC-225-22-Yb made by Crystal Fibre (Birkerod, Denmark). The fiber pump may for example be a model 4800, 4 W, Uncooled, Multi-Mode pump module from JDS Uniphase, of San Jose, Calif.

Figure 5:
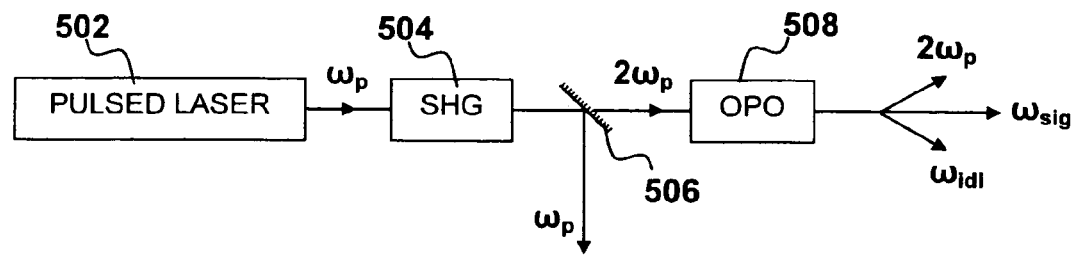
FIG. 5 is an example of a source of three wavelengths using an Optical Parametric Oscillator for use with embodiments of the present invention.

As discussed above, the optical source 202 may include produce the correlated photons by optical parametric oscillation. FIG. 5 is an example of such an optical source 500. The source 500 generally includes a pulsed laser 502, a second harmonic generator (SHG) 504, a dichroic mirror 506 and an optical parametric oscillator (OPO) 508. The pulsed laser produces pump radiation at a frequency $\omega_p$. The second harmonic generator interacts with the pump radiation to produce second harmonic radiation at double the frequency of the pump radiation, i.e., at $2\omega_p$. The SHG 504 may be less than 100% efficient at doubling the frequency of the pump radiation. The dichroic mirror 506 deflects pump radiation that makes it through the SHG 504. In the OPO 508, some of the second harmonic radiation is converted to signal and idler radiation, respectively at frequencies $\omega_{sig}$ and $\omega_{idl}$ that are related by:

$$2\omega_p = \omega_{sig} + \omega_{idl}$$

The pulsed laser 502 may be of any of the types described above. The second harmonic generator may be a non-linear crystal of any of the types described above phased matched for second harmonic generation. The OPO 508 may be a non-linear crystal of any of the types described above phased matched for optical parametric oscillation. The source 500 has the advantage of being tunable by virtue of the OPO phase matching. The phase matching is typically-tuned by adjusting e.g., the angle of the non-linear crystal used in the OPO, or by changing its temperature. Alternatively the poling period may be adjusted in periodically poled materials to phase match at different wavelengths.

Figure 6:
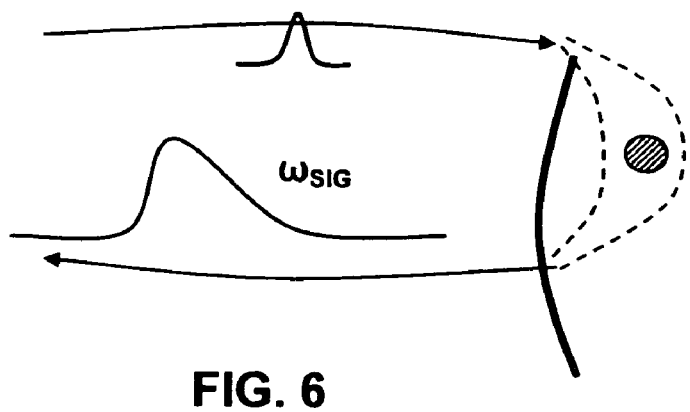
FIG. 6 is a schematic diagram illustrating an example of signal broadening expected at a tissue boundary.

Radiation pulses from the source 200 may be affected by traveling through tissue. For example, FIG. 6 is a schematic diagram of the signal expected at the tissue boundary TB shown in FIG. 2B. Injected pulses of radiation at frequency $\omega_{INJ}$ with a short pulse widths (e.g., about 1 to 50 picoseconds) are delivered into the body 201 at the tissue boundary TB. An injected pulse interacts with tissues in the body and emerges as a signal pulse at an optical frequency $\omega_{SIG}$, which may be slightly different from $\omega_{INJ}$ as a result of interaction with the ultrasound pulse. However any frequency shift occurring as a result of interaction between the optical pulses and the ultrasound pulses will be insignificant compared to the natural linewidth of the picosecond laser pulse as a result of the time-bandwidth constraint which derives directly from the Heisenberg Uncertainty Principle. Furthermore detection of this ultrasound-induced frequency shift is not required in the proposed embodiments of the invention, distinguishing this technique from those in the prior art. The signal pulse is typically broadened (e.g., to a pulse width of several hundred picoseconds to several nanoseconds) compared to the injected pulse due to the random-walk nature of photon propagation in turbid media, as shown by Turner et al., "Complete-angle projection diffuse optical tomography by use of early photons", Opt. Lett. 30(4), 409-411 (2005). This random walk increases the effective pathlength considerably. The time at which the photon arrives at the tissue boundary may be related to its approximate pathlength through mathematical relationships, for example the diffusion approximation or the Transport Equation.

Figure 7:
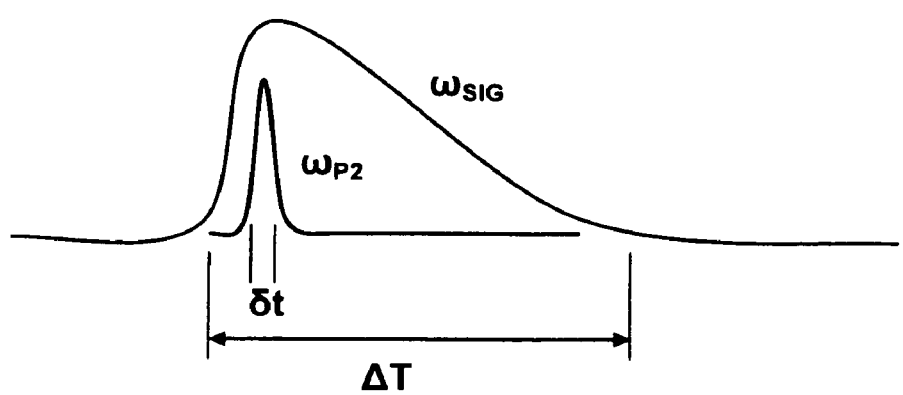
FIG. 7 is a schematic diagram of an apparatus using the principle of time gated upconversion according an alternative embodiment of the present invention.

The pulse spreading described above must be taken into account in time-gated detection of the signal pulse. One possible approach to taking such pulse spreading into account utilizes a technique referred to herein as time gated upconversion. FIG. 7 is a schematic diagram illustrating the principle of time gated upconversion. The broadened signal pulse at $\omega_{SIG}$ emerging from the tissue boundary TB with a pulse width $\Delta T$ of, e.g., a few nanoseconds, is mixed with a short mixing pulse (e.g., pulse width $\delta t$ of order several picoseconds) of radiation at an optical frequency $\omega_{P2}$. A master oscillator or a secondary slave oscillator may provide the short mixing pulse at $\omega_{P2}$. The mixing takes place in an upconverter such as a fiber OPA or a mixing crystal. Mixing can only occur when the two pulses are temporally and physically overlapped, so by strobing the mixing pulse through the emerging signal pulse it is possible to time gate the signal that is to be detected. This upconversion process may be accomplished in a manner that is highly efficient as described by Langrock et al., "Sum-frequency generation in a PPLN waveguide for efficient single-photon detection at communication wavelengths", Stanford Photonics Research Center Annual Report (2003) D-19-D-21, which is incorporated herein by reference.

Figure 8:
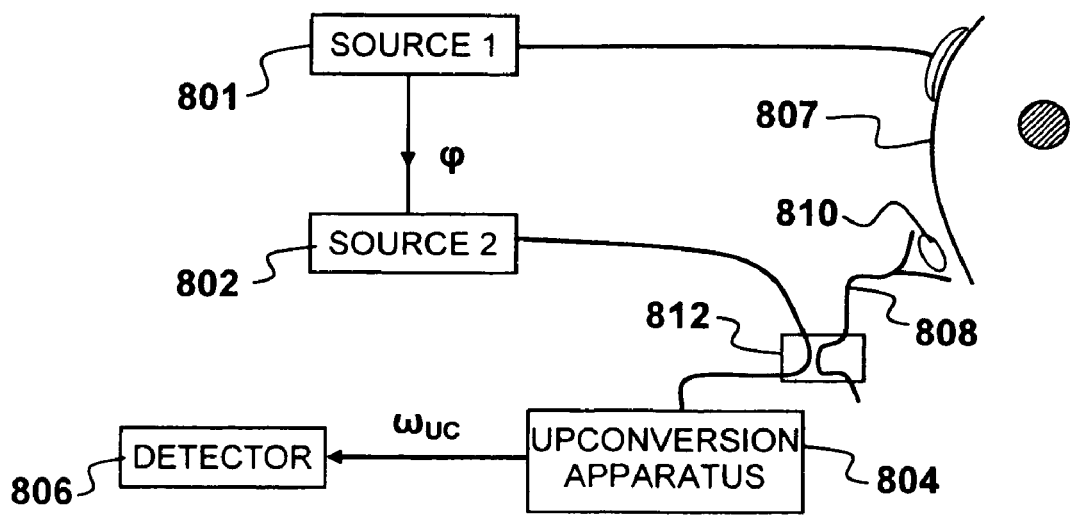
FIG. 8 is a schematic diagram of an apparatus having two pulsed optical sources according another alternative embodiment of the present invention proposed implementation of the present invention.

FIG. 8 is a schematic diagram illustrating of an alternative optical signal generation and detection apparatus 800 for use with embodiments of the present invention. The apparatus 800 includes first and second pulsed optical sources 801, 802 that respectively produce pulsed optical signals at optical frequencies $\omega_{P1}$ and $\omega_{P2}$. The first source 801 serves as a master oscillator for timing purposes and its output is used in one of the aforementioned processes to create two or more pulses of light at two or more wavelengths selected per the criteria described above. A timing signal $\phi$ is derived from the first source 801 and used to trigger the second source 802, which operates at substantially the same pulse repetition rate as the first source 801, but with an adjustable delay (phase angle) between the two pulse trains. The pulse train from the second source 802 is mixed in an upconversion apparatus 804 with the emerging signal at optical frequency $\omega_{SIG}$ from a tissue boundary 807 and the time delay between the two sources is adjusted to temporally gate the resulting signal, which is detected at a detector 806. This permits background-free, time-gated analysis of the emerging signal. The resulting upconverted signal may have an optical frequency $\omega_{UC}$ of $\omega_{P2} + \omega_{SIG}$ or $2\omega_{P2} - \omega_{SIG}$ depending on the nature of the upconversion apparatus 804. The two signals may be mixed, e.g., using a relay fiber 808 coupled to collection optics 810 and a 2×2 coupler 812 coupled to the relay optics and the second source 802.

Figure 9A:
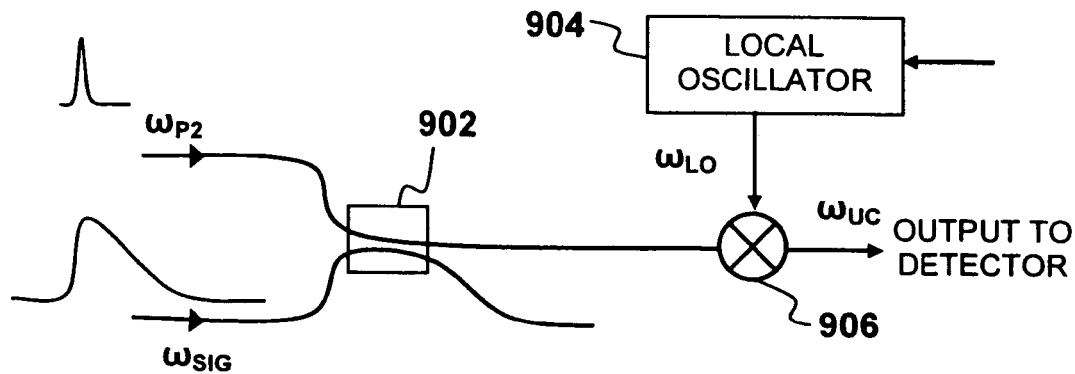
FIG. 9A is a schematic diagram depicting time-gated upconversion detector that can be used in the apparatus of FIG. 8.

In some embodiments, the upconversion apparatus 804 may include a local oscillator, e.g., a laser for time-gated upconversion. For example, as depicted in FIG. 9A, the signal pulse at $\omega_{SIG}$ and mixing pulse at $\omega_{P2}$ are combined, e.g., using a 2×2 coupler 902. Upconversion as described above may then be used to create a new signal photon wave at either $\omega_{P2} + \omega_{SIG}$ or $2\omega_{P2} - \omega_{SIG}$. A local oscillator laser 904 produces a pulsed wave at an optical frequency $\omega_{LO}$ and a repetition rate correlated to the ultrasound tone burst that is mixed in a mixing stage 906 with the new signal pulses before detection, generating a composite wave at optical frequency $\omega_{UC}$ given by either $(\omega_{P2} + \omega_{SIG} + \omega_{LO})$ or $(2\omega_{P2} - \omega_{SIG} + \omega_{LO})$ that is coupled to the detector 210. The mixing stage 906 may be a waveguide of for example a PPLN or PP-SLT, or a crystal of KTP or other material with high optical non-linearity. In this manner a signal may be generated that is temporally selected for an effective pathlength in the tissue. Upconverting the signal from the near-IR (around 1 micron) to the visible (400-700 nm) in this manner allows the use of silicon-based detector technology that has several advantages over InGaAs technology as discussed by Langrock et al. For example benefits include greater receiver sensitivity and lower dark counts from the detector.

The signal may be further selected for a temporal relationship to the modulating ultrasound tone burst from the transducer 206 by triggering the local oscillator 904 with an appropriate reference signal from the ultrasound source 207. For example by triggering the local oscillator 904 at twice the repetition rate of the tone burst, one can make a direct on/off comparison between the signal coming back from the tissue in the presence of, and absent the effect of the mechanical modulation.

Figure 9B:
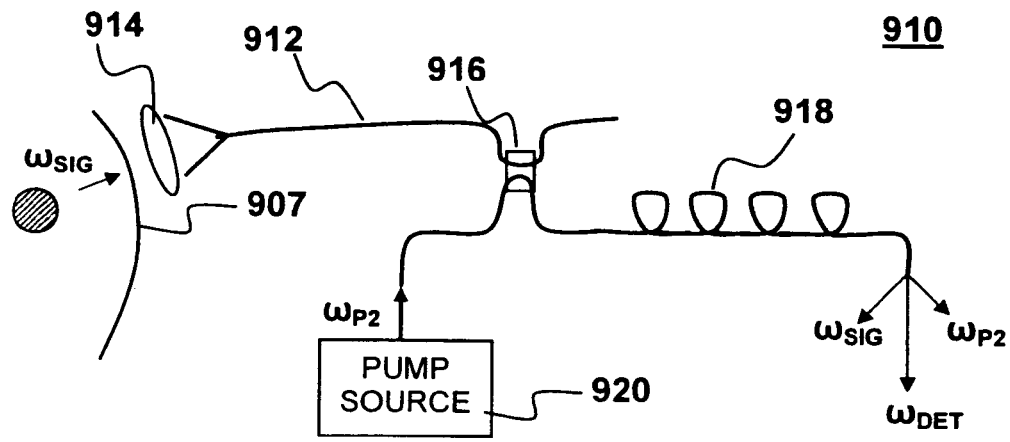
FIG. 9B is a schematic diagram depicting an alternative time-gated upconversion detector that can be used in the apparatus of FIG. 8.

Alternatively, the upconversion apparatus 804 may provide background free time gated amplification of the signal pulse. This may alternatively be accomplished using fiber Optical Parametric Amplification, e.g., as depicted in FIG. 9B. In an OPA-based background-free time-gated upconversion detector 910, optical signals at optical frequency $\omega_{SIG}$ emerging at a tissue boundary 907 are coupled into a relay fiber 912 by collection optics 914. The emerging optical signals at $\omega_{SIG}$ are then mixed (e.g., using a 2×2 coupler 916) into a Highly Non-Linear Fiber (HNLF) 918 with a drive pulse at optical frequency $\omega_{P2}$ from a pump source 920. The drive frequency $\omega_P$ may be provided by a high repetition rate mode-locked picosecond laser, such as the picoTRAIN™ series compact, all-diode-pumped, solid state picosecond oscillator manufactured by High-Q lasers of Kaiser-Franz-Josef-Str. 61 A-6845 Hohenems Austria or a mode-locked fiber laser, such as the picosecond version of the Femtolite™ D-200 from IMRA America Inc., Ann Arbor, Mich. 48105. The signal at $\omega_{SIG}$ is converted to a detected signal at $\omega_{DET}$ by an Optical Parametric Amplification (OPA) process in the fiber 918. The OPA process creates the detectable signal $\omega_{DET}$, e.g., through a four-wave mixing process described by:

$$\omega_{DET} = 2\omega_{P2} - \omega_{SIG}$$

Since the upconversion process only happens when the drive pulse at $\omega_{P2}$ is present the upconversion can be time gated. It should be noted that the frequency $\omega_{DET}$ of the detected signal is higher than either the signal or drive frequencies respectively. This means that the signal detected at frequency $\omega_{DET}$ will be substantially free of contaminating signals, e.g., from tissue autofluorescence (which always occurs to longer wavelength than the excitation wavelength), inelastic scattering internal to the fiber (Raman scattering for example) which is also always to longer wavelength than the fundamental, and other non-linear inelastic processes. By delaying the onset of the mixing or upconversion pulse used in the detection stage (802, 920), and then lengthening it in time using for example the all-electronic source shown in FIG. 4, we may adjust the detector to:

a) eliminate signal from photons which could not have interacted with the target, and b) include all possible contributions from photons which could have interacted with the target. This is equivalent to applying a Heaviside (step) function to the detected signal.

The aforementioned detection method may be more efficient compared to slowly moving a short upconversion/mixing pulse through the temporally broadened signal (FIGS. 6 and 7) by varying the delay as this latter technique implicitly selects a small subset of the photon trajectories, ignoring other possible contributions.

The detected signal may be amplified in a time gated manner by selecting a delay between the signal at $\omega_{P1}$ from the tissue boundary to be amplified and the drive pulse at $\omega_{P2}$. The drive pulse may be part of the beam from a master laser or may preferably be produced by a second pulsed laser operating at similar repetition rate and pulsewidth to the master oscillator. The amplification of a particular segment of the returning signal may also be selected by overlapping the two signals in time using a variable delay line. Using this technique, the signal at $\omega_{P1}$ will also be amplified by gains of for example 10-60 dB, as described by Ho et al. and references therein, allowing very weak signals to be detected.

Figure 10:
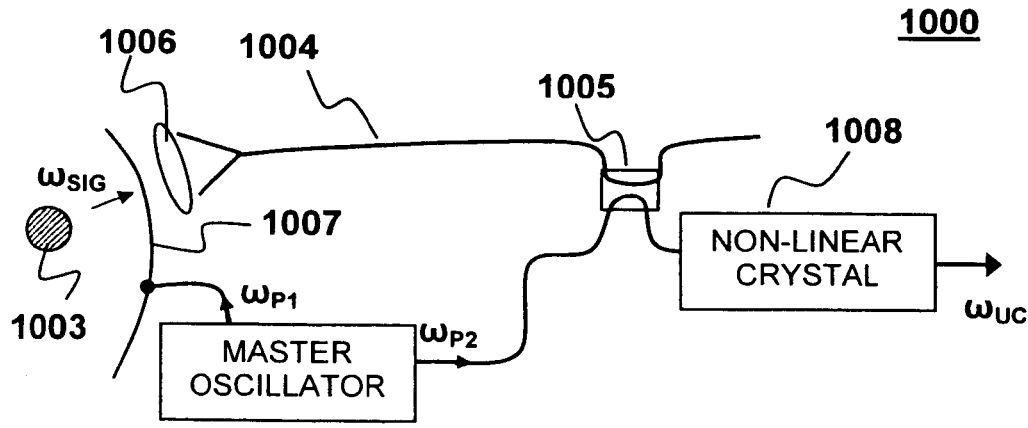
FIG. 10 is a schematic diagram depicting a second apparatus having a background-free time-gated upconversion detector according to another embodiment of the present invention.

Other background-free time-gated upconversion detection schemes can be implemented. For example FIG. 10 depicts an alternative background-free time-gated upconversion detector 1000. In the detector 1000 a master oscillator 1002 produces a first master oscillator pulse at an optical frequency $\omega_{P1}$. The first master oscillator pulse is used to generate temporally correlated photons (e.g., as described above) that are scattered from a target tissue 1003 within a body 1001 to provide a signal. Signal photons at an optical frequency $\omega_{SIG}$ emerging from a tissue boundary 1007 are coupled into a fiber 1004, e.g., via relay optics 1006. After amplification in a doped section of the fiber 1004, the signal photons are mixed (e.g., using a 2×2 coupler 1005) in a non-linear crystal 1008 with a second time-delayed master oscillator pulse having an optical frequency $\omega_{P2}$. The non-linear crystal 1008 is phase matched for frequency mixing of the signal photons and the second oscillator pulse. The resulting upconverted signal is characterized by an optical frequency $\omega_{UC}$ given by:

$$\omega_{UC} = \omega_{P2} + \omega_{SIG}$$

A temporal delay between the first and second oscillator pulses is adjusted such that the time evolution of the signal emerging from the tissue boundary can be probed. This allows early arrival photons, which could not have interacted with the target by virtue of their arrival time, to be gated out.

It should be understood that the signals referred to above generally include two or more signal photons of different wavelengths that are detected in coincidence. Coincidence detection of the two signal photons can be accomplished by balanced photoreceivers, for example New Focus (Bookham) model 1807 and 1817, San Jose, Calif. The wavelengths of interest can be isolated by interference filters such as the RazorEdge™ and MaxLine™ Laser and Raman filters from Semrock, Inc. of Rochester, N.Y. Alternatively coincident photon pairs or multiplets can be detected using high speed analog and digital electronics, for example time correlated single photon counting equipment such as the SPC-134 from Becker and Hickl GmbH, Berlin, Germany, or boxcar integrators such as the Model SR200 Boxcar from Stanford Research Systems, Sunnyvale, Calif.

The time-gated amplified signal is analyzed to reveal the component being modulated at the radiation-pressure modulation frequency $\omega_{RPM}$. This can be accomplished using lock-in detection using for example a lock-in amplifier (e.g., a Stanford Research Systems SRS Model 844) as the filter 212 in FIG. 2A.

The remaining signal by virtue of the above generation and detection techniques must have:

a) Interacted with the target structure being modulated by the radiation pressure field, b) Been generated by photons at each of the two or more selected wavelengths which traveled approximately the same path length from the launch site, through the target being modulated, and back to the detector.

The two or more wavelengths of the correlated photons provided by the optical source 202 may be selected to have different affinities for the various states of hemoglobin (oxy-Hb, met-Hb, deoxy-Hb). The arrival of correlated photons at the different wavelengths therefore can be interpreted to indicate for example the oxygenation level or pH of the blood in the modulated target structure. For example, if one radiation-pressure modulates a blood vessel and its contents, and illuminates the area with two wavelengths of light, one selectively absorbed by oxy-hemoglobin and one substantially less selectively absorbed, the arrival rate of correlated photon pairs will be higher if they traverse a radiation-pressure-modulated vascularized area containing high levels of deoxy-Hb (because one of the pair will be selectively more absorbed in areas of higher oxygen saturation). By way of example 1030-nm radiation is absorbed more strongly by oxy-hemoglobin than 1064-nm radiation. Similarly, 1100-nm is more strongly absorbed by oxy-hemoglobin than 1064-nm radiation. These three wavelengths may be conveniently generated as shown above. They also have the added attraction of having substantially similar elastic scattering coefficients, which will lead to a simplification in calculation of the effective pathlength each traverses. They also have substantially similar absorption in water, leading to a simplification in assessing the potential contribution for error in the measurement caused by non-hemoglobin related absorption of the probe wavelengths.

Figure 11:
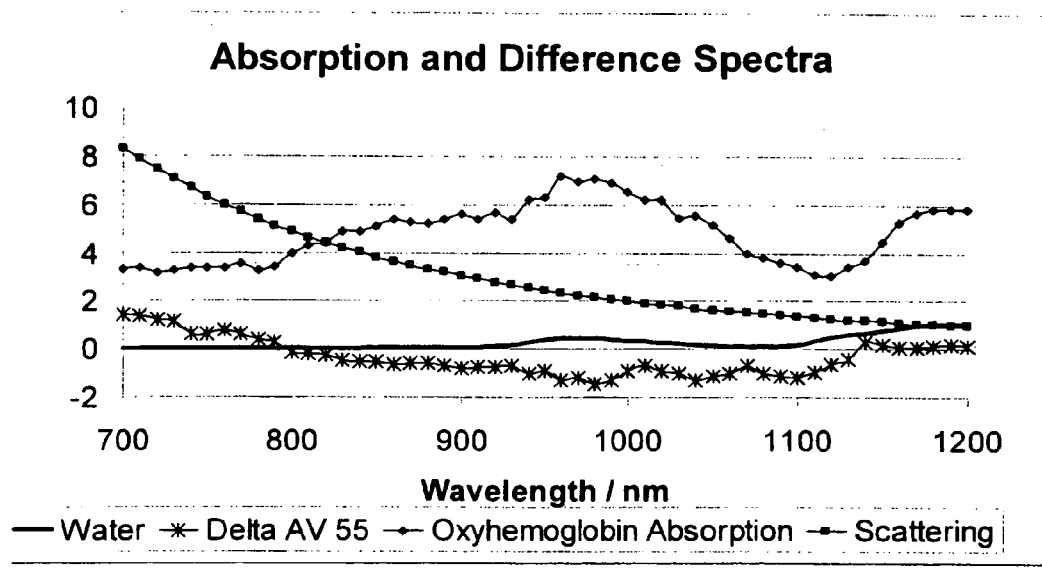
FIG. 11 is a graph of the absorption of oxy-hemoglobin and water in the range 700-1200 nm, an expected variation of the scattering coefficient as a function of wavelength, and an expected difference between an artery with fully oxygen-saturated blood and a vein where the oxygen saturation is 55%.

FIG. 11 is a graph showing the absorption of oxyhemoglobin (diamonds) and water (solid curve) in the range 700-1200 nm, the nominal variation of the scattering coefficient as a function of wavelength (squares), and the expected difference in absorption between an artery with fully oxygen-saturated blood ($SaO_2$=100) and a representative vein where the oxygen saturation is 55% (asterisks—Delta AV 55). The points at which the difference curve crosses Y=0 are known as isosbestic points. There are two isosbestic points in the absorption spectra of oxy-hemoglobin and deoxy-hemoglobin, one around 810 nm and one around 1135 nm. At these wavelengths the absorption of blood in the vessel is independent of oxygen saturation. These points are known to be useful for internal reference calibration, for example to exclude the effects of volume changes in the absorption resulting from pulsatile flow from the heart.

The wavelength range 1025-1135 nm is characterized by having reduced absorption as the venous oxygen saturation decreases. This means that the signal derived as described in the embodiments of the present invention will increase with decreasing saturation in this wavelength range. The gradient of the absorption change with respect to oxygen saturation at the 1135 nm isosbestic point is also very steep, much more so than at 810 nm, making it of significant potential value. Around this wavelength range, we may make sensitive measurements at two or more wavelengths on each side of the isosbestic point. The sign of the absorption change will change from one side of the isosbestic point to the other.

The scattering function in FIG. 11 varies as the inverse fourth power of the wavelength. This means that longer wavelengths (for example from 1025 nm-1150 nm are not as affected by scattering as shorter wavelengths from for example 700-930 nm). This translates to a smaller increase in the effective pathlength resulting from elastic scattering. The scattering function in the 1025 nm-1150 nm also does not vary significantly, indicating that if we probe the target using wavelengths in this range we may regard scattering as a secondary effect and model it as a perturbation. This is not true in the 700-930 nm range, where the scattering function varies by more than a factor of three.

The wavelength range 1025-1150 nm has rich structure in the difference spectrum, has much lower scattering than the visible and near-IR wavelength ranges, and has relatively modest water absorption. This region offers several convenient and readily available laser sources (Nd:YAG, Yb:Fiber lasers) which are known from dermatology to have excellent penetration properties into tissue.

It is possible to bias the selection of wavelengths to enhance the diagnostic value of the measurement. For example, fetal oxygenation levels are known to be substantially lower than the conjugate maternal levels. Thus, the selection of wavelengths can be biased to probe the fetus preferentially over the mother. Furthermore, if it is desired to detect the pH of the blood in the ultrasound-modulated target, one can inject probe photons at a frequency known to be selective for met-hemoglobin absorption. For example in the wavelength range from 800-1350 nm met-hemoglobin has much stronger absorption than either oxy-hemoglobin or deoxy-hemoglobin as shown in Kuenster J. T and Norris K. H. "Spectrophotometry of human hemoglobin in the near infrared region from 1000 to 2500 nm", J. Near Infrared Spectrosc. 259-65 (1994). The wavelength range 1000-1300 nm and especially from 1100-1250 nm is particularly sensitive to met-hemoglobin absorption. The absorption spectrum of met-hemoglobin is known to be sensitive to pH, as shown for example in Zijlstra et al., "Visible and Near Infrared Absorption Spectra of Human and Animal Haemoglobin, $1^{st}$ ed. Utrecht: VSP Publishing; 2000, page 62, and one may thus infer the pH of the target from the coincidence arrival rate of appropriately chosen photon pairs or triplets or higher multiplets.

Embodiments of the present invention are distinguishable from Diffuse Optical Tomography, where the signal detected has subsumed within it all possible absorbers in the path of the field and no attempt is made to localize the absorber location. The present technique is further distinguished from the various practices of ultrasound-tagged optical spectroscopy because it does not detect small frequency shifts or speckles on the emerging photons. Instead, the present technique detects the modulation imparted by physical motion of the target, which in turn affects the optical absorption cross-section. The present invention is insensitive to the very short speckle decorrelation time caused by blood flow in the vessel, which would otherwise severely complicate the detection of modulated photons in interferometric or frequency-domain techniques. The present modulation technique occurs at much higher frequency than other motion artifacts, for example pulsatile flow from the heart beat, allowing it to be decoupled in the signal analysis. This is important when, for example, the technique is used to perform trans-abdominal fetal oxygenation measurements where it is desirable to distinguish the maternal and fetal oxygenation systems.

There are many possible designs for sensors that may be used in embodiments of the present invention. For example, FIG. 12A depicts an example of a sensor 1200 for transdermal measurements. The sensor 1200 generally includes a substrate 1202, which may be made of a flexible plastic or similar material. A thin ultrasound transducer 1204 is mounted on or embedded within the substrate. The transducer 1204 receives power from an ultrasound transmitter and sends return signals through a cable 1205. Optical signals are transmitted and received through an optical fiber bundle 1206 containing launch and receive fibers terminated with coupling optics 1208. The launch/receive fibers and coupling optics 1208 may be mounted to or embedded with the substrate 1202, proximate the transducer 1204. The launch/receive fibers may be used to both transmit and receive optical signals. The fibers and coupling optics 1208 are distributed in a more or less planar fashion. This type of sensor may be used for transdermal measurements.

FIG. 12B depicts an alternative sensor 1210 that is a variation on the sensor shown in FIG. 12A. A transducer 1214, launch fibers and optics 1218, collection fibers and optics 1219 are mounted to or embedded within a substrate 1212 in a more or less planar fashion. In this example, the transducer 1214 is disposed between the launch fibers and the collection fibers. The transducer 1214 receives power from an ultrasound transmitter and sends return signals through a cable 1215. The launch fibers and optics 1218 receive optical radiation from a source via a fiber bundle 1216. The collection fibers and optics 1219 transmit signals to a detector via another fiber bundle 1217.

Other sensor configurations may be useful for trans-esophageal or trans-tracheal measurements. For example, FIGS. 12C-12D depict a sensor 1220 that may be inserted into the esophagus or the trachea. The sensor 1220 includes a ring-shaped substrate 1222 made of a bio-compatible material. Two or more ultrasound transducers (or transducer arrays) 1224 are mounted to the substrate 1222. The transducers are arranged to emit ultrasound in an outward fashion as indicated by the arrows depicted in FIG. 12D. The transducers receive and transmit signals through a cable 1225. Arrays of launch/receive fibers 1228 are disposed on or embedded within the substrate 1222 proximate the transducers 1224. The launch/receive fibers 1228 receive and/or transmit optical signals via a fiber bundle 1226. The ring-shaped sensor 1220 may be placed in the esophagus. Alternatively, the sensor 1220 may be placed in the left or right bronchus, through the trachea, e.g., at the end of a tube that provides oxygen to the patient. Alternatively, the sensor 1220 may be implanted into the patient's trachea and providing a read out to small portable monitoring unit for continuous ambulatory monitoring.

Use of the sensors and apparatus described above for monitoring of blood oxygenation can be accomplished in a variety of different ways.

Figure 13:
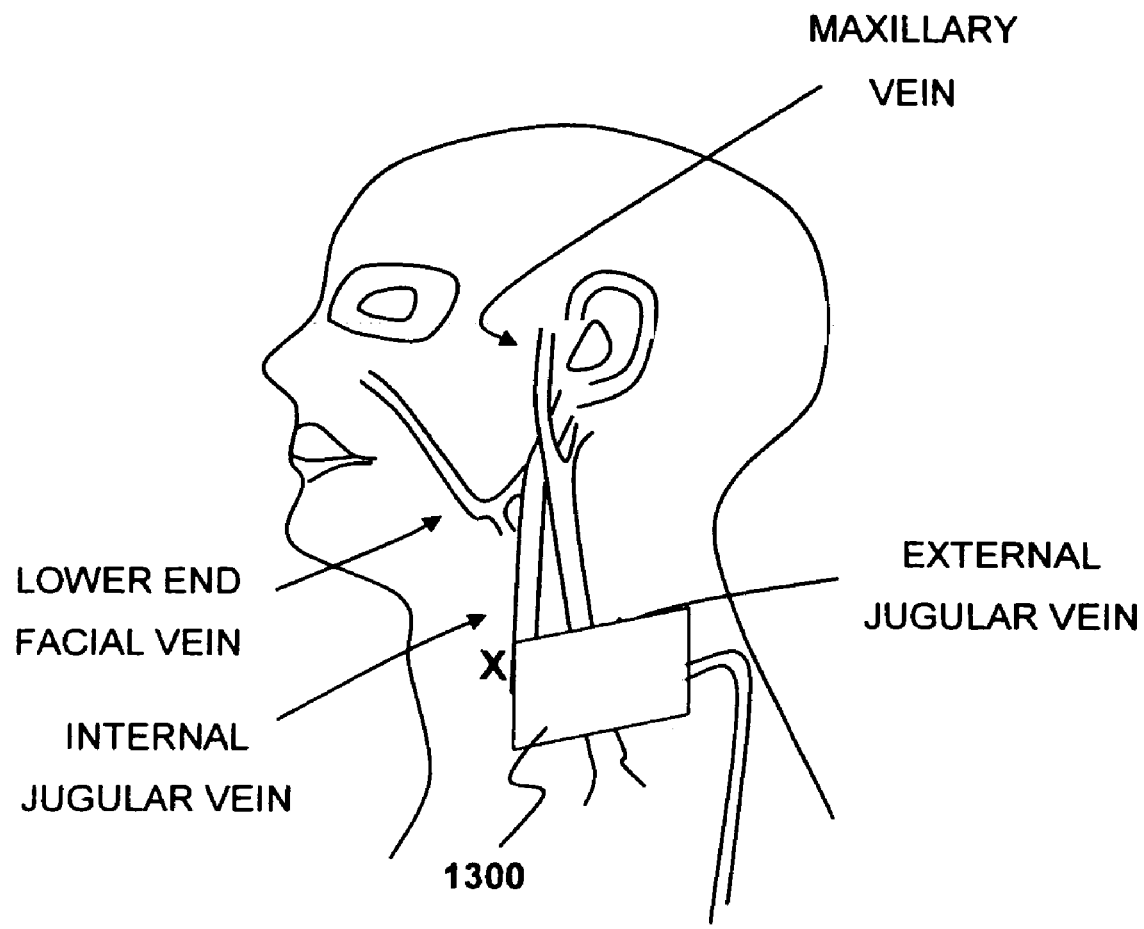
FIG. 13 is a schematic diagram illustrating an example of trans-dermal measurement of oxygenation of blood the internal or external jugular veins.

For example, FIG. 13 illustrates a simple case of transdermal measurements of oxygenation in the interior or exterior jugular vein of a patient. A sensor 1300, e.g., of the type depicted in FIG. 12A or FIG. 12B may be placed against the patient's neck in the vicinity of the spot marked with an X. The sensor 1300 may be coupled to a remote unit of the type described above with respect to FIG. 2A. Venous oxygen saturation in the jugular vein can be measured using the ultrasound/optical technique described above while arterial oxygenation can be measured using standard pulse oximetry. Cardiac output can then be calculated from the Fick principle as described above. Alternatively arterial saturation may be measured by radiation-pressure modulating the carotid artery instead of the internal jugular vein. Although a single sensor 1300 is depicted on one side of the of the neck, two or more such sensors (or one large sensor) may be placed on the dermis simultaneously on the left and right side of the neck over both internal jugular veins.

Figure 14:
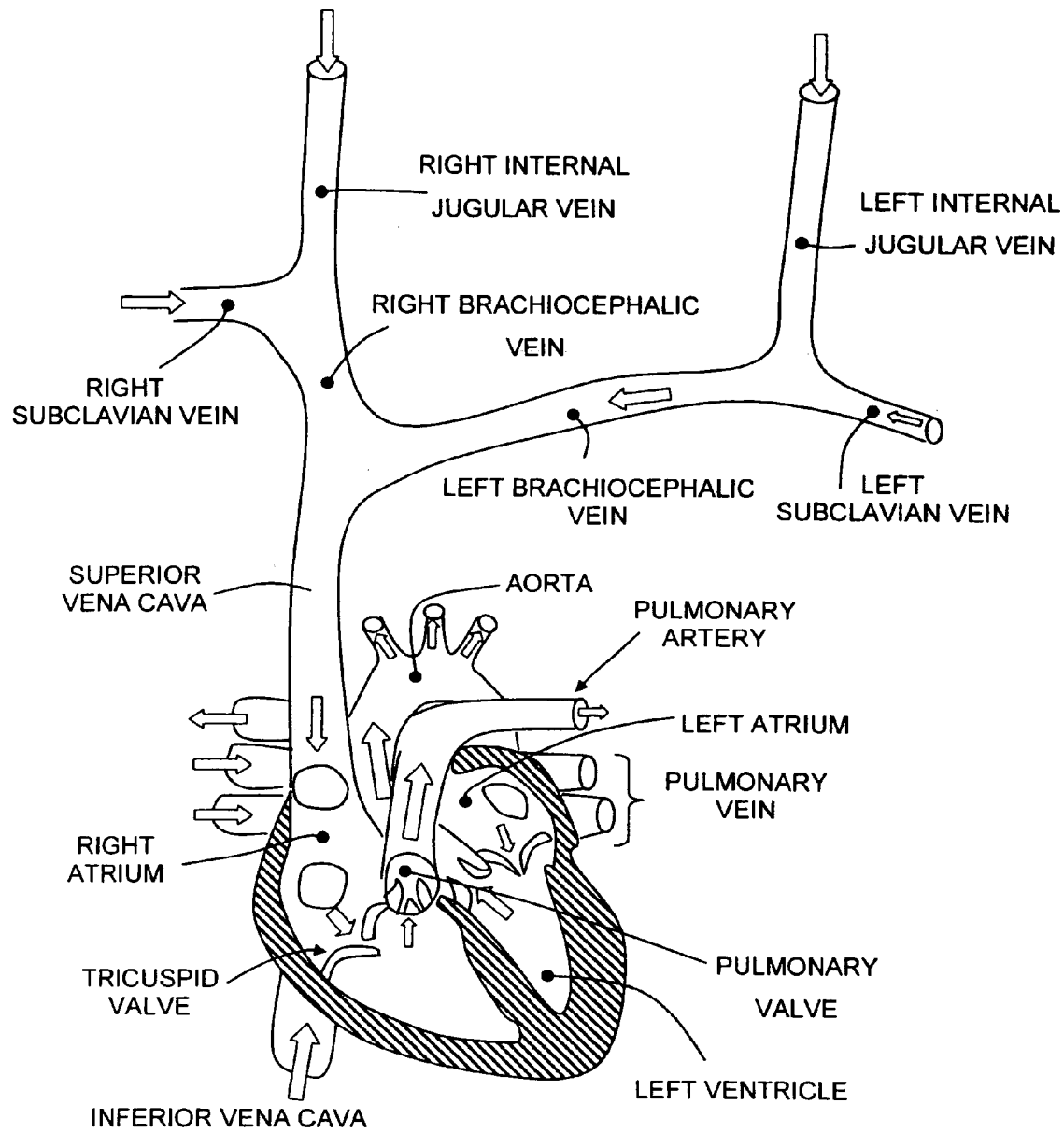
FIG. 14 is a schematic diagram of a portion of the circulatory system showing examples of locations that may be probed for blood oxygenation using embodiments of the present invention.
Figure 15:
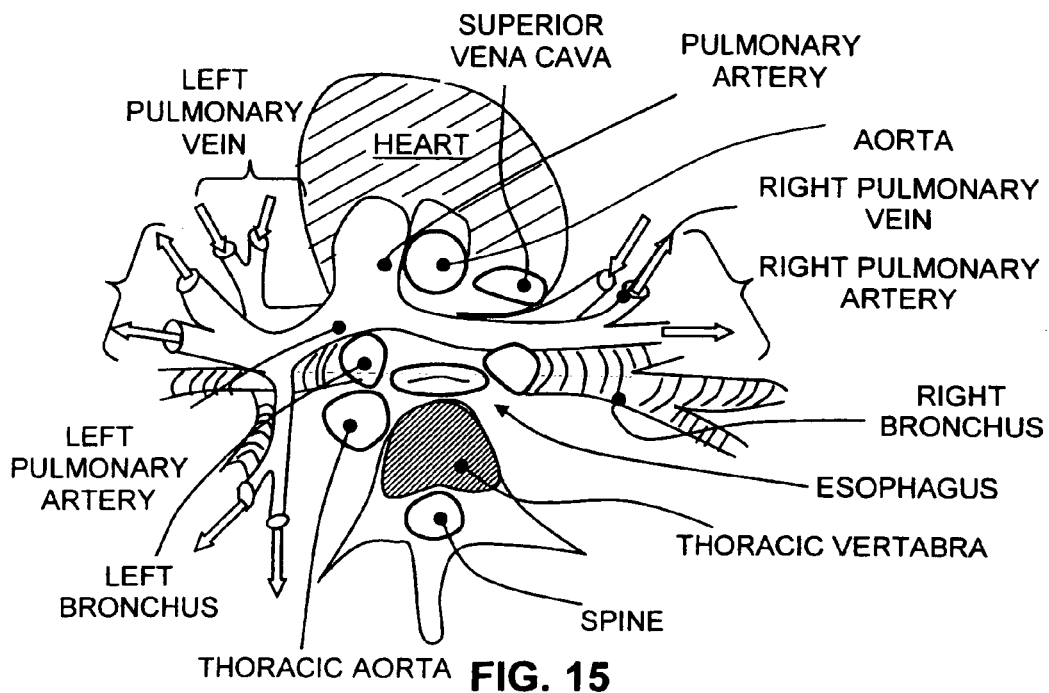
FIG. 15 is a horizontal cross-section through the chest showing examples of showing examples of locations that may be probed for blood oxygenation using embodiments of the present invention.
Figure 16:
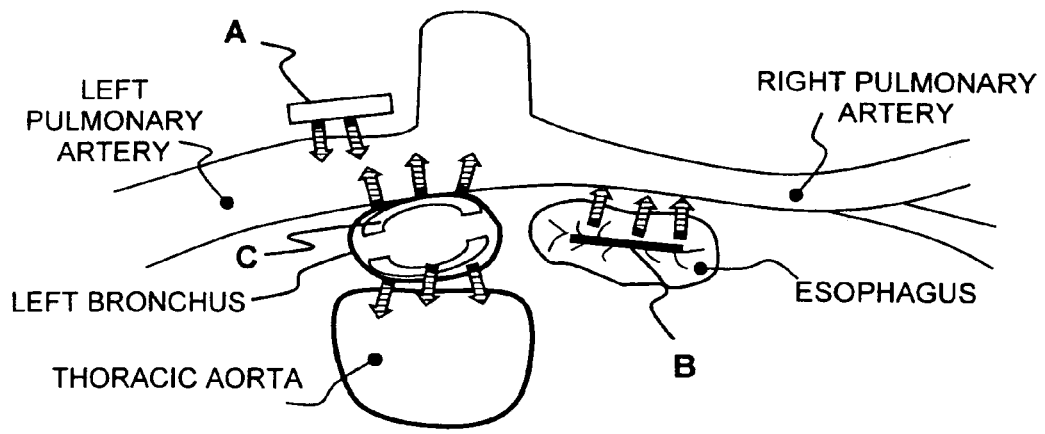
FIG. 16 is a close-up vertical thoracic cross-section illustrating a sensor placed in the left bronchus to probe oxygenation of the left pulmonary artery and descending thoracic aorta.

There are a number of different targets within the body that are suitable for blood oxygen monitoring using embodiments of the present invention. These can be understood with reference to the anatomical diagrams of FIG. 14 and FIG. 15. For example, both right and left internal jugular veins are potential targets as described above. Measuring both simultaneously would probably be a superior method. FIG. 16 illustrates three other possible sensor placements that may be used in conjunction with embodiments of the present invention. First, a sensor A may be inserted using a bronchoscope between two ribs (an intercostal space) next to the sternum. In this case the sensor could be positioned right up against the pulmonary artery (probably away from the aorta). This is the optimum place to make the measurement of venous oxygen saturation assuming that there are no defects in the heart. For example, if there is an acquired ventricular septal defect, in which blood is short-circuited from left ventricle to right ventricle, the oxygen saturation of the pulmonary artery is abnormally high (e.g., about 80, whereas the incoming blood from the jugular vein may be around 50). Such a condition would result in a false reading for the cardiac output measured using the Fick principle. However an alternative probe site on the internal jugular vein gives an adjunct measure of the cardiac output independent of heart defects. So the two measurements would be complimentary.

Figure 17:
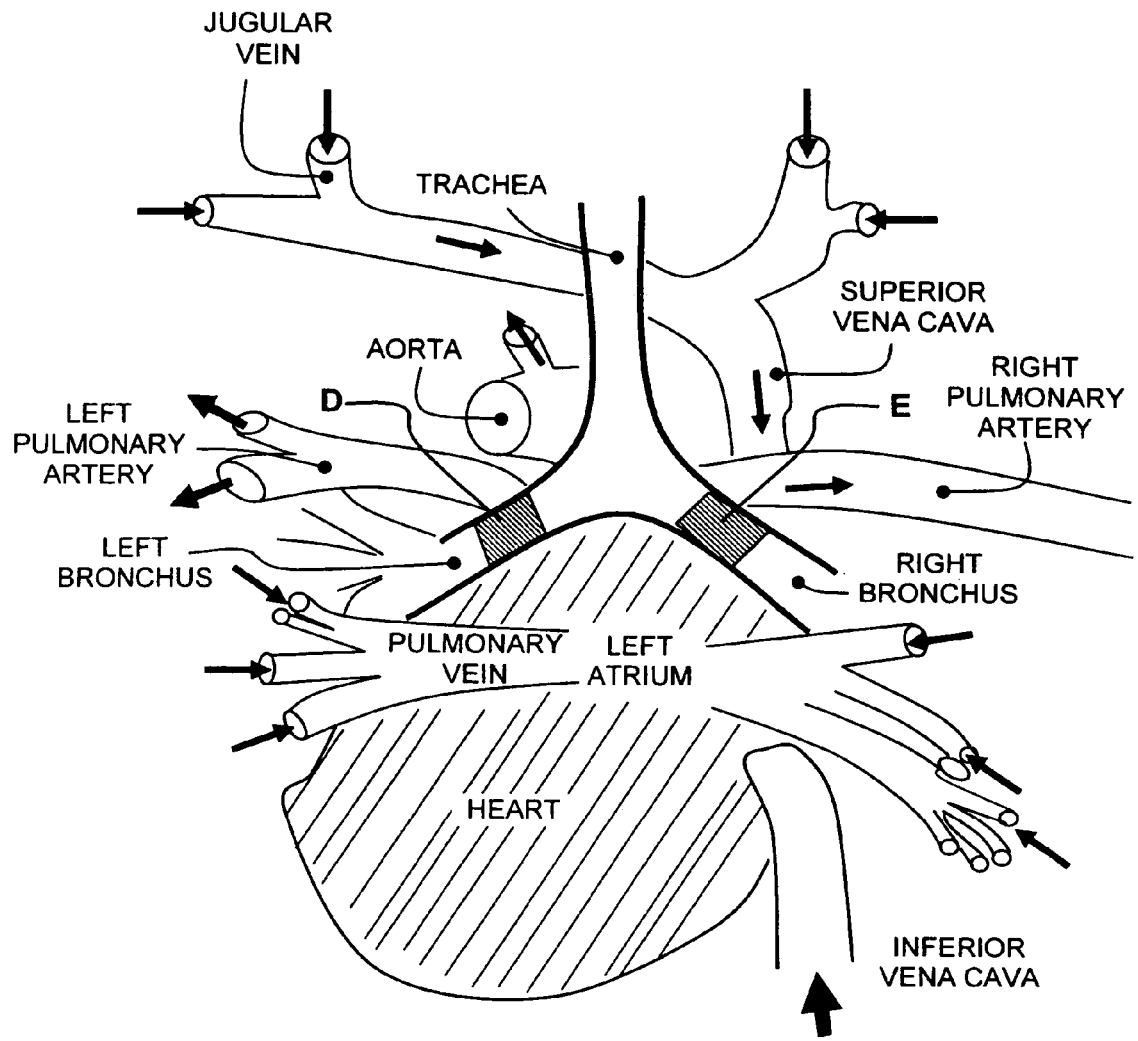
FIG. 17 is a schematic thoracic diagram illustrating an example of trans-tracheal placement of a sensor according to an embodiment of the present invention.

Alternatively, as shown in FIG. 16, a sensor B may be placed in the esophagus. The sensor B may be of the planar type depicted in FIG. 12A or FIG. 12B or the ring type depicted in FIGS. 12C-12D. A sensor C may also be placed in the left bronchus via the trachea. These two probes will also sample the pulmonary arteries. The trans-esophageal probe will sample the right pulmonary artery. The trans-tracheal (bronchial) sensor C will potentially be able to simultaneously probe the oxygen saturation in both the left pulmonary artery (the venous saturation) and the descending thoracic aorta (arterial saturation). This would eliminate the need for external pulse oximetry to measure the arterial oxygen saturation. Positioning of a sensor D within the left bronchus or a sensor E within the right bronchus is illustrated in the dorsal pull-away view of FIG. 17. Such trans-tracheal sensors may be the ring-shaped sensor of the type depicted in FIGS. 12C-12D. The sensors A, B, C, D, E may be coupled to a remote unit of the type described above with respect to FIG. 2A. Optical and ultrasound signals can probe the chemistry of the cardiovascular system in the manner described above.

Embodiments of the present invention also have application to monitoring of neonatal blood oxygenation. Monitoring of neonatal blood oxygenation is particularly useful in the cases of neonatal heart defects as illustrated in FIGS. 18A-18C. FIG. 18A depicts an example of a normal heart. Certain patients exhibit a heart defect known as Patent Ductus Arteriosus (PDA). As illustrated in FIG. 18B, PDA is the persistence of a normal fetal structure (indicated by the arrow) between the left pulmonary artery and the descending aorta. Persistence of this fetal structure beyond 10 days of life is considered abnormal. Other patients exhibit a defect known as Patent Foramen Ovale (PFO). As shown in FIG. 18C, PFO is a persistent opening in the wall of the heart (indicated by the arrow) which did not close completely after birth. The opening is required before birth for transfer of oxygenated blood via the umbilical cord. This opening can cause a shunt of blood from right to left, but more often there is a movement of blood from the left side of the heart (high pressure) to the right side of the heart (low pressure). Normally this opening closes in the first year of life; however in about 30% of adults a small patent foramen ovale is still present. Diagnosis of both PDA and PFO may be helped by measurement of venous oxygen saturation.

In newborn infants (neonates) the distance across the thorax may be small enough that in addition to trans-esophageal and trans-tracheal, and trans-dermal for the internal jugular, it may be possible to operate the diagnostic apparatus transdermally with a sensor placed directly on a neonate's chest surface. The sensor, e.g., of the planar type depicted in FIGS. 12A-12B, is placed proximate the heart or a blood vessel of interest. The target area is a neonatal cardiovascular system. As illustrated in the cross-sectional diagram of FIG. 19 the measurement may be made in either a reflection mode or trans-illumination mode (in one side—out the other). In the reflection mode, optical signals are transmitted and received via a common sensor 1902. In the trans-illumination mode a transmitter unit 1904 sends optical signals through an infant's thorax. Scattered photons of radiation from these signals are collected by one or more sensors 1906, 1908 that are positioned to probe radiation scattered from particular structures within the neonatal anatomy such as the pulmonary artery. The sensors 1906, 1908 may be coupled to a remote unit of the type described above with respect to FIG. 2A. Optical and ultrasound signals can probe the chemistry of the neonatal cardiovascular system in the manner described above.

Figure 20:
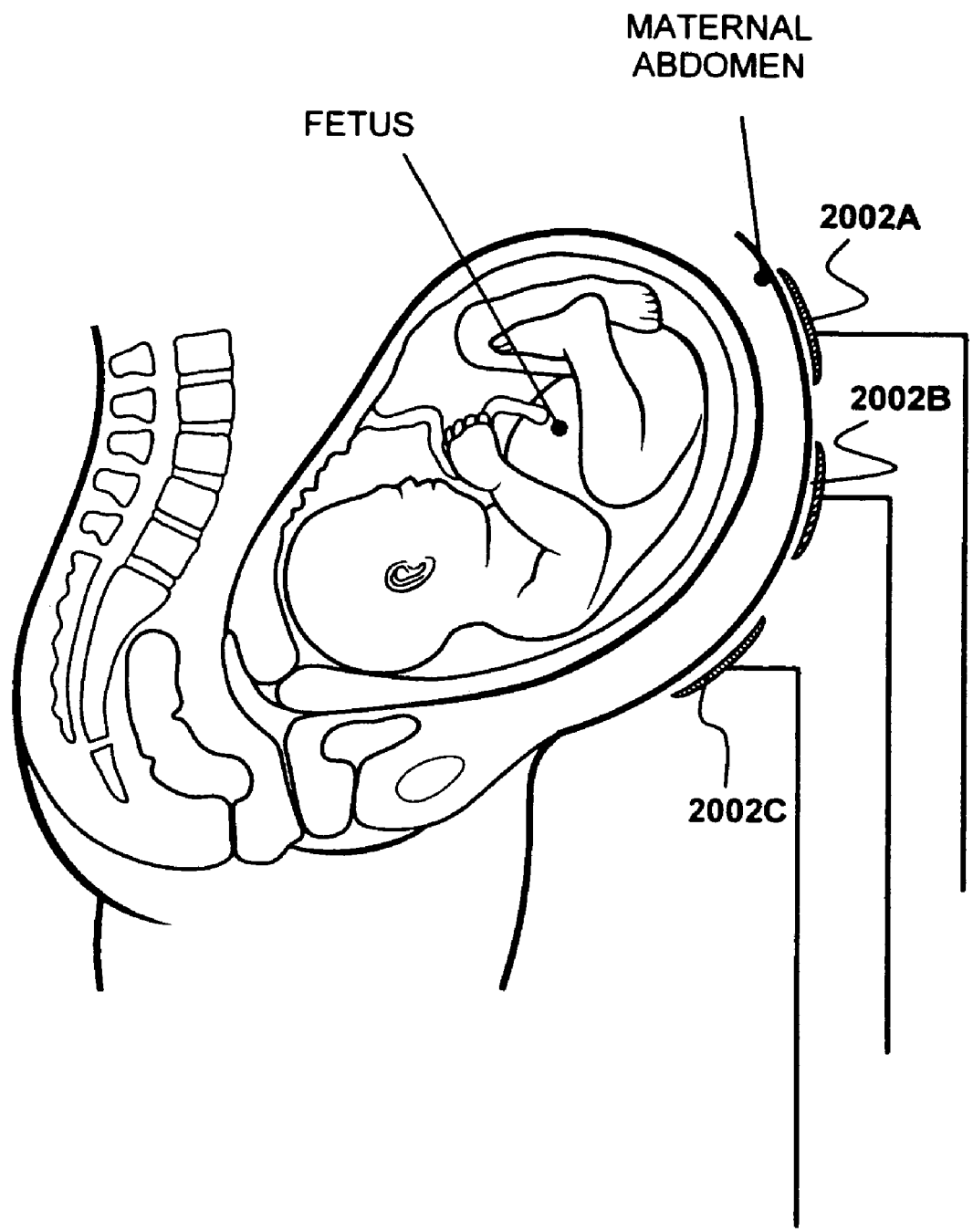
FIG. 20 is a sagittal cross-sectional schematic diagram illustrating examples of sensor placement for monitoring of fetal blood oxygenation.

Further embodiments of the invention include using diagnostic apparatus of the type described herein for fetal monitoring. For example, as depicted in FIG. 20, one or more sensors 2002A, 2002B, 2002C, e.g., planar sensors of the type depicted in FIGS. 12A-12B, may be placed on a pregnant woman's abdomen to probe the fetal cardiovascular system. The sensors 2002A, 2002B, 2002C may be coupled to a remote unit of the type described above with respect to FIG. 2A. Optical and ultrasound signals can probe the chemistry of the fetal cardiovascular system in the manner described above. In this case, the target area is the fetal oxygen exchange system, including the placenta, placental vasculature, fetal heart and major fetal blood vessels. Such transabdominal fetal monitoring can provide information about fetal blood oxygenation levels in a minimally invasive or non-invasive manner. Fetal oxygenation levels are known to be substantially lower than the conjugate maternal levels. The selection of wavelengths used can be biased to probe the fetus preferentially over the mother.

A further embodiment of the invention will now be described relating generally to non-invasive optical systems and methods for determining the trends of the ratio of oxygenated and deoxygenated hemoglobin and other parameters, such as pH, in blood vessels such as the internal jugular vein (IJ), and/or the carotid artery.

Near-infrared spectroscopy has been used for non-invasive measurement of various physiological properties in animal and human subjects. The basic principle underlying the near-infrared spectroscopy is that physiological tissue is a relatively highly scattering medium and is a relatively low absorbing medium to the near-infrared waves. Many substances in a medium may interact or interfere with the near-infrared light waves propagating therethrough. Human tissues, for example, include numerous chromophores such as oxygenated hemoglobin, deoxygenated hemoglobin, water, lipid, etc, where the hemoglobin is the dominant chromophores in the spectrum range of 700 nm to 900 nm. Accordingly, the near-infrared spectroscope has been conventionally applied to measure the trend in oxygen levels of blood in the physiological medium.

Various techniques have been developed for the near-infrared spectroscopy. Examples include: time-resolved spectroscopy (TRS), phase modulation spectroscopy (PMS), and continuous wave spectroscopy (CWS). The conventional NIRS spectroscopy techniques have been developed for measuring average blood oxygen saturation within a tissue volume which is the mixture of arterial, venous, and capillary blood. For the applications of monitoring cardiac output, blood saturation can be measured within the internal jugular vein. This is advantageous in many circumstances since the internal jugular vein is a major blood vessel surrounded by highly scattering tissue medium in the neck.

Advantageously, the present embodiment can separate or distinguish blood flow in the internal jugular vein from surrounding tissue medium, and can therefore more accurately measure the trends in internal jugular vein blood oxygen saturation. Additionally, the present invention can provide such measurements non-invasively using optical systems and determine the trends of the ratio of oxygenated and deoxygenated hemoglobin in internal jugular vein blood vessel.

Figure 21:
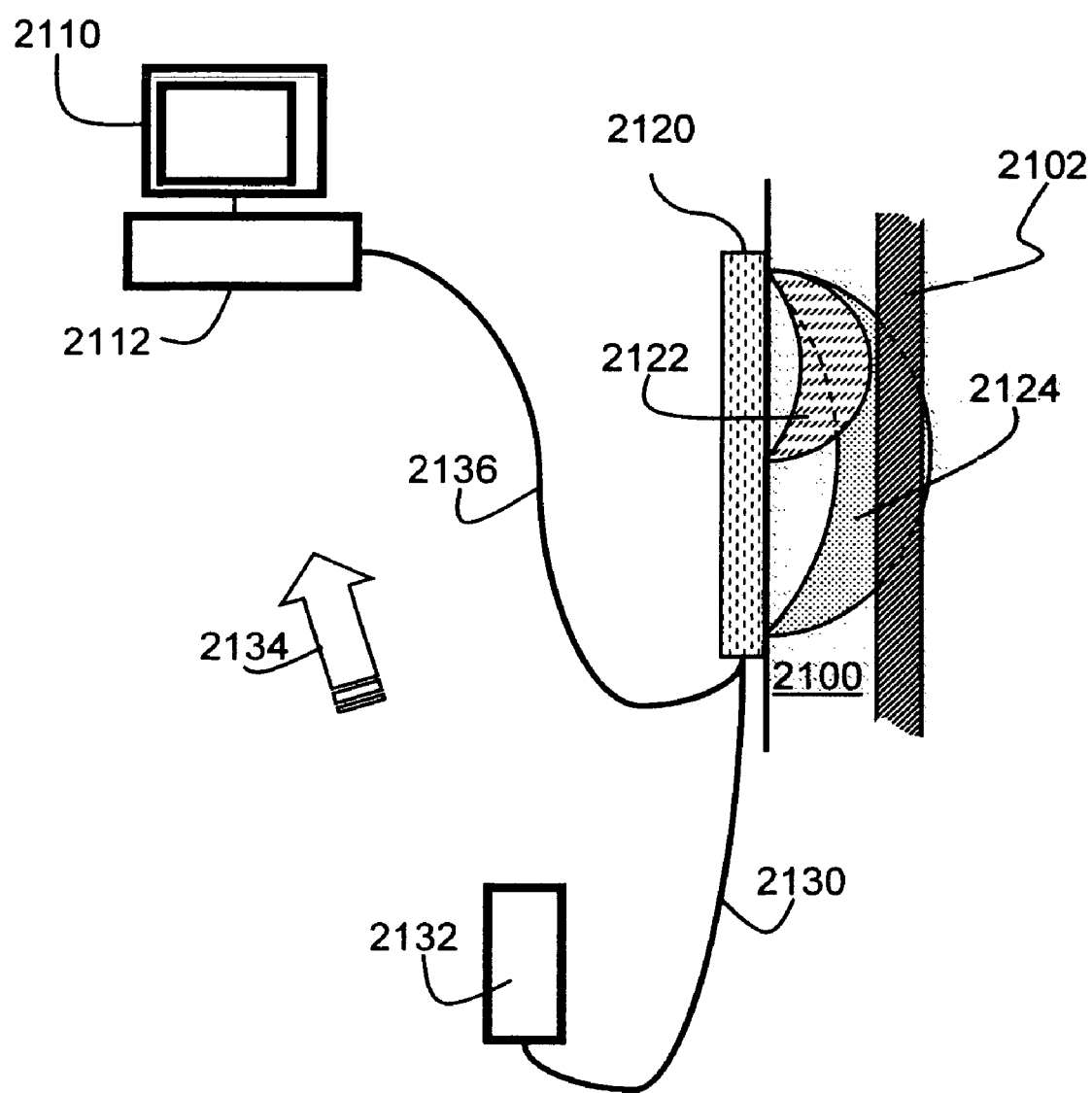
FIG. 21 is a system for making relative measurements relating to blood oxygenation and/or pH according to an embodiment of the invention.

FIG. 21 shows a system for making relative measurements relating to blood oxygenation according to an embodiment of the invention. As shown in FIG. 21, the system includes a patch sensor 2120 which can be reusable or disposable. Patch 2120 is made from a bio-compatible material, such as a suitable bio-compatible rubber, and is preferably attached to the skin of the patient using a bio-compatible adhesive. In some applications, the adhesive should be less permanent, so the patch can be repositioned. In other applications, the adhesive should be more permanent, to make measurements over longer periods of time. As described in further detail below, patch 2120 includes one or more electromagnetic radiation transmitters and one or more electromagnetic radiation detectors. The radiation from patch 2120 transmits into the body 2100, such as the tissues of the neck. The body 2100 includes a target blood vessel 2102 in which measurements related to blood oxygen saturation are taken. The target blood vessel 2102 can be more than 1 cm below the surface of the skin (or other tissue boundary) at the location where patch 2120 is engaged, and in many cases, such as where the target blood vessel is the internal jugular vein in an adult patient, vessel 2102 is typically about 2 cm below the skin. The crescent-shaped pathways 2122 and 2124 of the radiation transmitted by patch 2120 scattered through tissues of body 2100 and collected by the detectors has is shown. The transmitters and detectors are configured, arranged and/or positioned preferably such that the pathways include at least two different penetration depths. As shown in FIG. 21, pathway 2122 is shallower and does not include blood vessel 2102, whereas pathway 2124 is deeper and includes blood vessel 2102. Note that the two different depths are achieved in the system of FIG. 21 preferably by two different transmitter/detector pair separation distances.

Optical fiber cables or electronic wire cables 2130 and 2136 connect the patch 2120 to either a main station box 2112, or to a portable unit 2132 which sends out data through wireless communication to station box 2112 as illustrated by arrow 2134. In communication with station box 2112, display 2110 shows both time course trend and digits of oxygen saturation in the blood vessel(s) of interest, e.g. the internal jugular vein and/or carotid artery, as wells as oxygen consumption rate. Portable unit 2132 is preferably dimensioned and sized such the patient can carry the portable box for extended periods.

Figure 22:
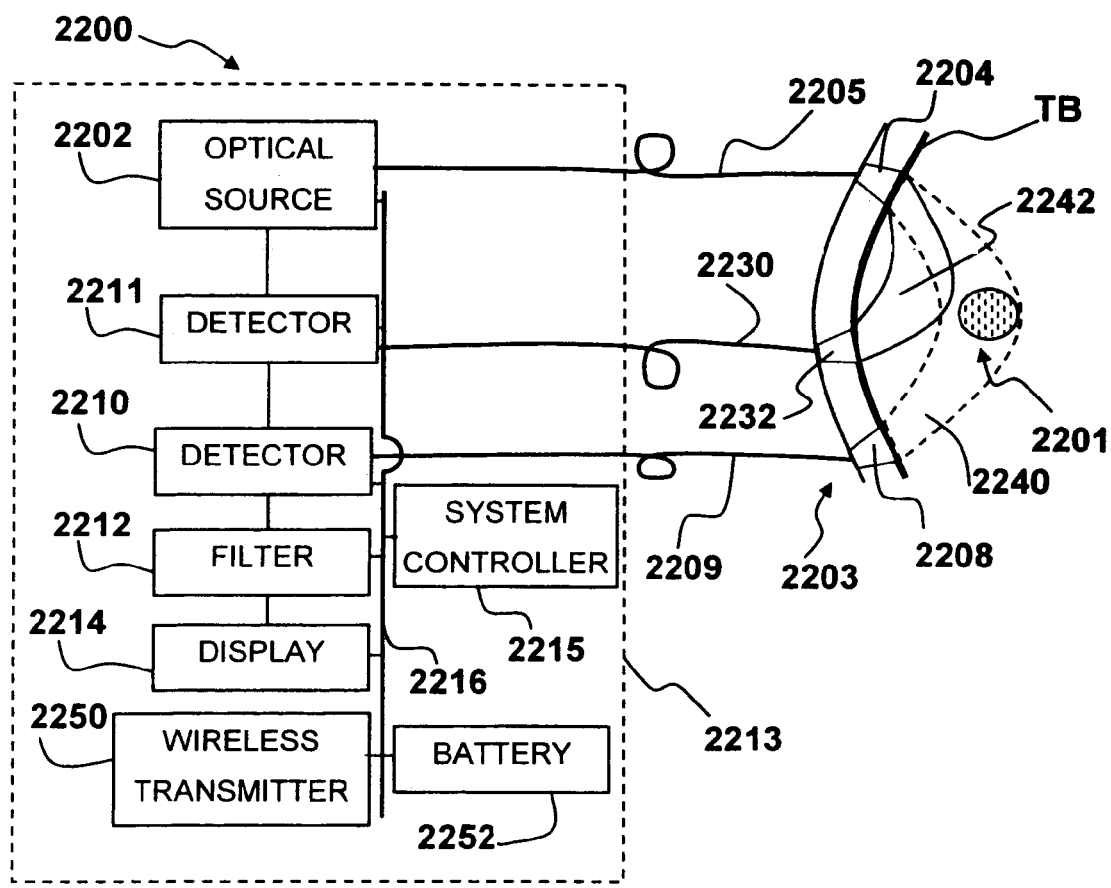
FIG. 22 is a schematic block diagram of a monitoring system according to an embodiment of the invention.

FIG. 22 is a schematic block diagram of a monitoring system according to an embodiment of the invention. The apparatus 2200 is similar in many respects to apparatus 200 as shown in FIG. 2A and FIG. 2B and described above. Apparatus 2200 generally includes an optical source 2202, launch optics 2204, collection optics 2208 and 2232, optical detectors 2210 and 2211, associated electronics such as a filter 2212, an optional display 2214, optional wireless transmitter 2250 and optional battery 2252. The optical source 2202 provides pulsed or continuous electromagnetic radiation. The launch optics 2204 may include one or more optical fibers 2205 that couple the electromagnetic radiation from the optical source 2202 to tissues within tissue boundary TB. Similarly, the collecting optics 2208 and 2232 collect optical signals reflected from within the tissues. Shallow pathway 2242 shows the region of radiation travel from source 2204 to collecting optics 2232. Deep pathway 2240 shows the region of radiation travel from source 2204 to collecting optics 2208. Note that shallow pathway 2242 substantially excludes blood vessel 2201, and preferably does not include blood vessel 2201, whereas deep pathway 2240 includes blood vessel 2201. The collecting optics 2208 and 2232 may include one or more optical fibers 2209 and 2230 respectively, that couple signals scattered electromagnetic radiation to the optical detectors 2210 and 2211 respectively.

Launch optics 2204 and collecting optics 2208 and 2232 are preferably mounted together on a patch 2203. Note that patch 2203 is shown having the arrangement of the launch optics and optical detectors such that pathways 2240 and 2242 are perpendicular to blood vessel 2201. Alternatively, patch 2203 can be engaged such that the radiation pathways are parallel to the blood vessel, as shown for example in FIGS. 21 and 23, and in some cases such parallel engagement has been found to be preferable. Referring again to FIG. 22, in some embodiments, the optical source 2202, optical detectors 2110 and 2232, filter 2212 and display 2214 may be part of a station box 2213 coupled to the patch 2203 by fiberoptics 2205, 2209, 2230 and electrical cables. The station box 2213 may include a system controller 2215. The system controller 2215 may include a central processor unit (CPU) and a memory (e.g., RAM, DRAM, ROM, and the like). The controller 2215 may also include well-known support circuits, such as input/output (I/O) circuits, power supplies (P/S), a clock (CLK), Field Programmable Gate Arrays (FPGAs) and cache. The controller 2215 may optionally include a mass storage device such as a disk drive, CD-ROM drive, tape drive, or the like to store programs and/or data. The controller may also optionally include a user interface unit to facilitate interaction between the controller 2215 and a user. The user interface may include a keyboard, mouse, joystick, light pen or other device. The preceding components may exchange signals with each other via a controller bus. In addition, the optical source 2202, detectors 2210 and 2211, filter 212, and display 214 may exchange signals with the controller 2215 via the system bus 2216. Alternatively, 2213 could be a portable unit that includes battery 2252 and optional wireless transmitter 2250 for communicating with a separate station box. By using a portable unit arrangement, the patient is freer to move about, and the monitoring can take place over much longer periods of time than would otherwise be practical.

The controller 2215 typically operates the optical source, 2202, optical detectors 2210 and 2211, filter 2212 and display 2214 through the I/O circuits in response to data and program code instructions stored and retrieved by the memory and executed by the processor. The program code instructions may implement embodiments of the diagnostic technique described herein. The code may conform to any one of a number of different programming languages such as Assembly, C++, JAVA, Embedded Linux, or a number of other languages. The CPU forms a general-purpose computer that becomes a specific purpose computer when executing program code. Although the program code is described herein as being implemented in software and executed upon a general purpose computer, those skilled in the art will realize that the method of pulsed pumping could alternatively be implemented using hardware such as an application specific integrated circuit (ASIC) or FPGA or other hardware circuitry. As such, it should be understood that embodiments of the invention can be implemented, in whole or in part, in software, hardware or some combination of both.

Figure 23:
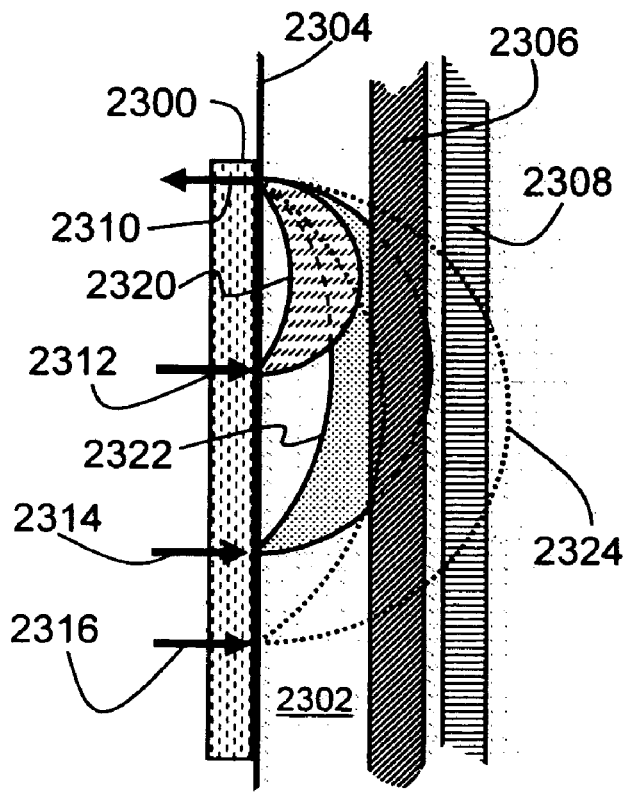
FIG. 23 is a side view of a monitoring patch placed in close proximity to tissues containing two blood vessels of interest, according to an embodiment of the invention.

FIG. 23 shows a side view of a monitoring patch placed in close proximity to tissues containing two blood vessels of interest, according to an embodiment of the invention. Patch 2300 is shown in side view attached, preferably adhered to tissue boundary 2304. Patch 2300 includes three electromagnetic radiation transmitters 2312, 2314 and 2316, as well as one electromagnetic radiation receiver 2310. By positioning the patch 2300 in the appropriate location, and due to the spacings between each of the transmitters 2312, 2314, and 2316 on the one hand and receiver 2310 on the other hand, three different pathways of electromagnetic radiation scattering 2320, 2322 and 2324 are produced within tissues 2302. Tissues 2302 include two blood vessels of interest 2306 and 2308. Through position of patch 2300 and transmitter/receiver spacing as described above, pathway 2320 includes tissues but substantially excludes both blood vessels 2306 and 2308. Likewise pathway 2322 includes blood vessel 2306 while substantially excluding blood vessel 2308, and pathway 2324 includes both blood vessels 2306 and 2308. Through processing described in more detail below and preferably performed in system controller 2215 in FIG. 22, relative measurements related to blood oxygenation in the two blood vessels can be made. Referring again to FIG. 23, according to a preferred embodiment, tissue 2302 is neck tissue and tissue boundary 2304 is the skin of the patient's neck. According to this embodiment, blood vessel 2306 is the internal jugular vein, and blood vessel 2308 is the carotid artery. Using processing as described above and more fully below, monitoring relating to blood oxygenation in the internal jugular vein and carotid artery can be obtained and cardiac output can be accurately calculated in a non-invasive manner. Additionally, if patch 2300 is made of a comfortable compliant material such as bio-compatible rubber and is adhered to the neck skin, the oxygenation measurements and cardiac output calculations can take place over a relatively long period of time. In cases where a portable box is used such as shown in FIG. 22 and described above, the patient need remain a the clinic or hospital location. In this way, the measurements and calculations can be performed continuously over a long periods, for example for several days, while the patient is performing a wide range of normal activities throughout each day.

As used herein, the term "pathway" or "pathways" for electromagnetic radiation or photons refers to the photon pathway spatial probability distribution, and the pathways depicted in the figures herein illustrate the approximate locations having a probability of 95% or greater.

As used herein with respect to pathways including or excluding certain structures such as blood vessels, the terms "substantial" or "substantially" mean that approximately 50% or more (or less than 50% in the case of excluding a structure) of the cross section of the structure at a particular longitudinal position falls within (or falls outside) the pathway. For example, the phrase "pathway 2242 substantially excludes blood vessel 2201" as used herein means that pathway 2242 includes less than 50% of blood vessel at the position in question. The phrase "pathway 2242 ... preferably does not include blood vessel 2201" as used herein means that preferably the photon pathway spatial probability distribution illustrated by pathway 2242, having a probability of 95% or greater does not include blood vessel 2201, or in other words, any spatial location within the blood vessel have a less than 5% photon spatial probability.

Figure 24:
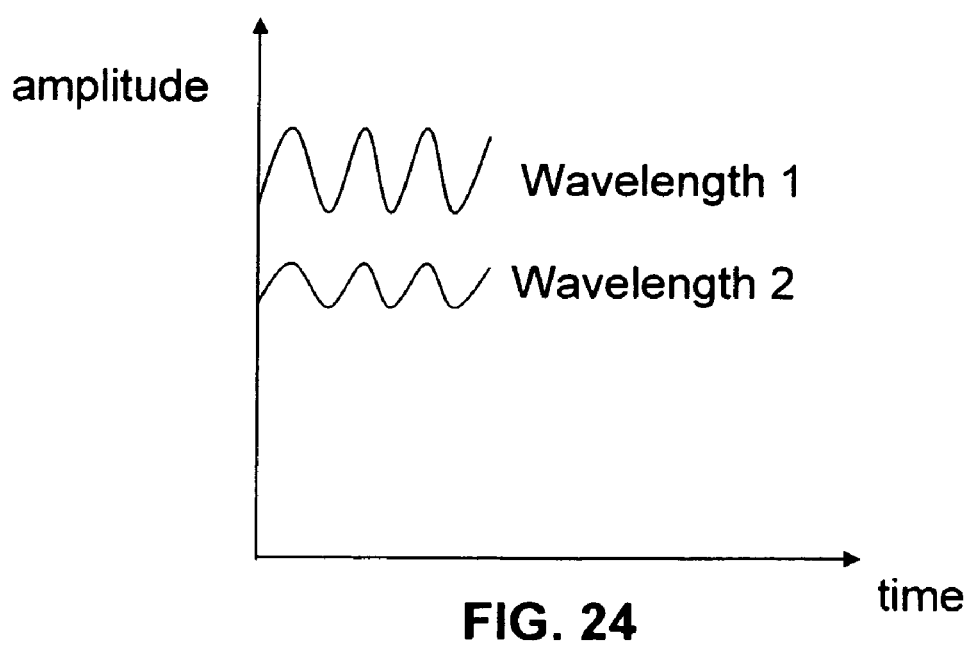
FIG. 24 illustrates amplitude modulation of two different wavelengths of electromagnetic radiation, according to an embodiment of the invention.

To distinguish between oxy-hemoglobin and deoxy-hemoglobin, as described above and shown in FIG. 11, at least two different wavelengths of light between 680 nm to 900 nm are transmitted from each source position to obtain the absorption properties of the blood vessel of interest at each wavelengths and to calculate blood oxygen saturation. FIG. 24 illustrates amplitude modulation of two different wavelengths of electromagnetic radiation, according to an embodiment of the invention. The amplitude of two different wavelengths of light are shown being modulated, for example as by the pulse of an artery in the case of radiation pathway 2324 in FIG. 23 being modulated by the pulse in carotid artery 2308.

Using the processing methods and apparatus as described above in the examples relating to ultrasound modulation, more accurate measurements relating to arterial oxygenation can be taken by making use of natural modulations due the pulse in arteries.

Figure 25A:
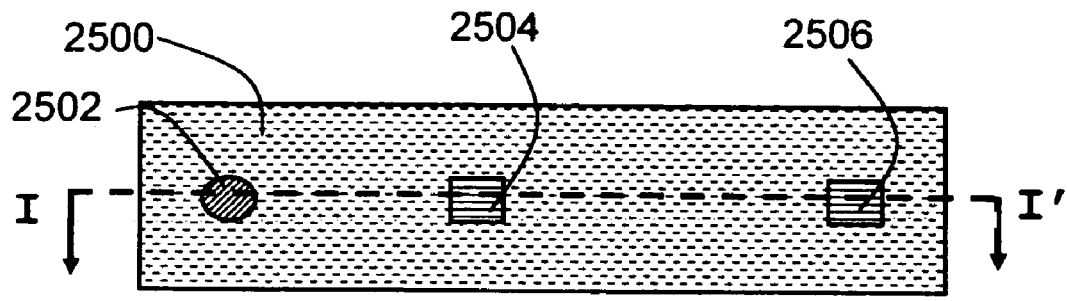
FIGS. 25a and 25b are top views of sensor patches according to embodiments of the invention.
Figure 25B:
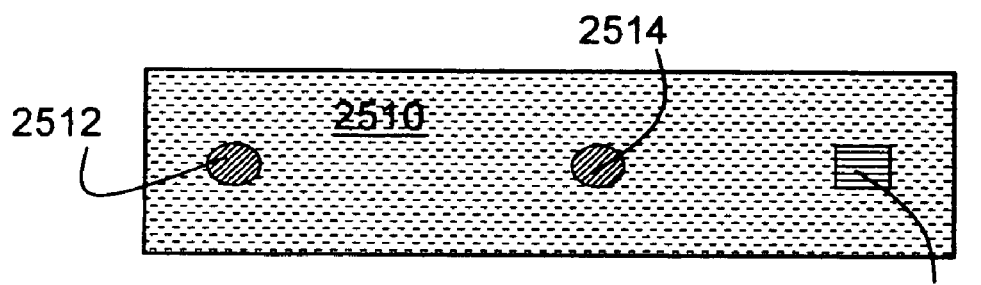

FIGS. 25a and 25b show a top view of sensor patches according to embodiments of the invention. FIG. 25a shows sensor patch 2500 including transmitter 2502, and two receivers 2504 and 2506. The spacing between the transmitter/receiver pairs should be chosen such that the depth of the resulting radiation pathway is appropriate for the particular application. For example, in some cases where patch 2500 is placed on the skin of the neck, and the shallower radiation pathway between transmitter 2502 and receiver 2504 is to include the superficial tissues of the neck but not the internal jugular vein, a spacing of about 2 cm has been found suitable, and the deeper pathway between transmitter 2502 and receiver 2506 is to include the superficial tissues as well as the internal jugular vein, a spacing of about 5 cm has been found suitable.

FIG. 25b shows sensor patch 2510 including two transmitters 2512 and 2514, and one receiver 2516. As described above, the spacing between the transmitter/receiver pairs should be chosen according to the particular application. In some cases of non-invasive neck monitoring of oxygenation in the internal jugular vein, it has been found that the shorter spacing (transmitter 2514 and receiver 2516) should be about 2 cm, and the longer spacing (transmitter 2512 and receiver 2516) should be about 5 cm. In cases, such as shown and described above with respect to FIG. 23, where the carotid artery will also be monitored, an even longer spacing should be provided and in some cases it has been found that a spacing of about 7 cm is suitable for making measurements on the carotid artery. The spacing for a particular case depends not only on the type and location of the blood vessel being monitored, but also in general on the individual size and body type of the patient. For example a child versus a large adult, and also the thickness and make up of the superficial tissue layers between the neck skin and the internal jugular vein and carotid artery. It has been found that in many cases the useful range of spacing should be between about 0.5 to 3 cm for a pathway that does not include the internal jugular vein, should be between; 3 to 7 cm for a pathway that includes the internal jugular vein but not the carotid artery; and 5 to 10 cm for a pathway that includes the carotid artery.

Figure 26:
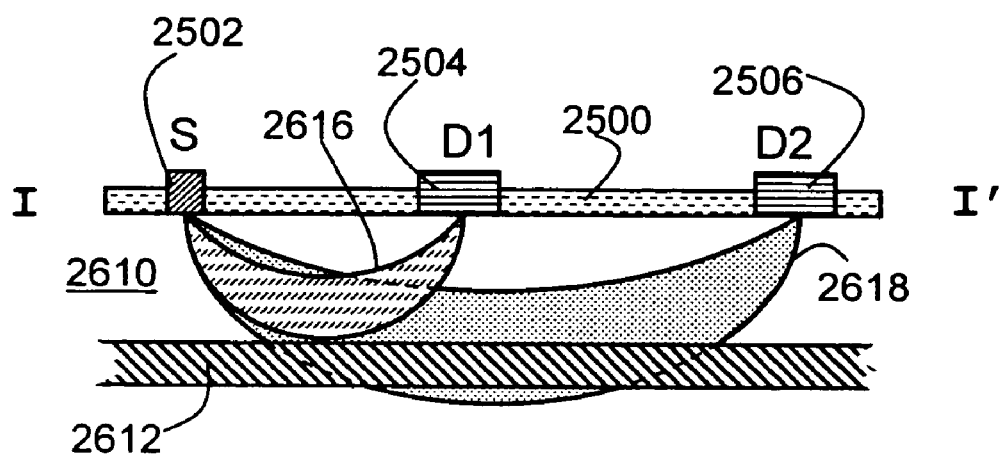
FIG. 26 is a cross section along I-I' of the sensor patch of FIG. 25a placed on tissues containing a blood vessel of interest, according to an embodiment of the invention.

FIG. 26 shows a cross section along I-I' of the sensor patch of FIG. 25a placed on tissues containing a blood vessel of interest, according to an embodiment of the invention. Patch 2500 contains a single sensor 2502 and two detectors 2504 and 2506 which generate two radiation pathways 2616 and 2618 within tissues 2610. Note that the shallower pathway 2616 includes the superficial tissues within 2610 but not blood vessel 2612, whereas pathway 2618 includes both the superficial tissues and the blood vessel 2612. Using the processing as described in greater detail below, parameters such as relative blood oxygenation in the blood vessel 2612, such as the internal jugular vein, can be monitored.

Figure 27A:
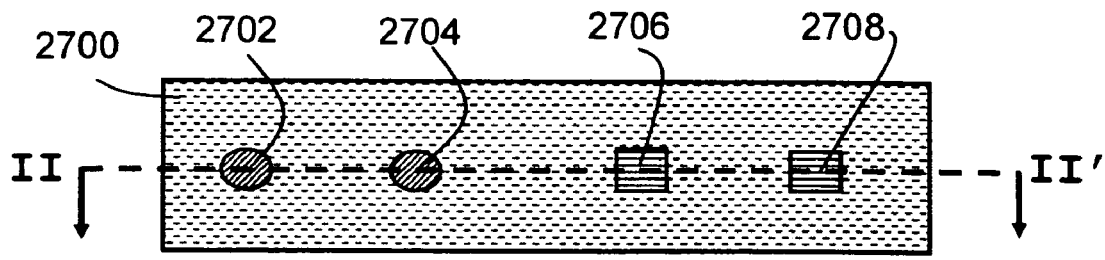
FIGS. 27a and 27b are plan views of sensor patches according to further embodiments of the invention.
Figure 27B:
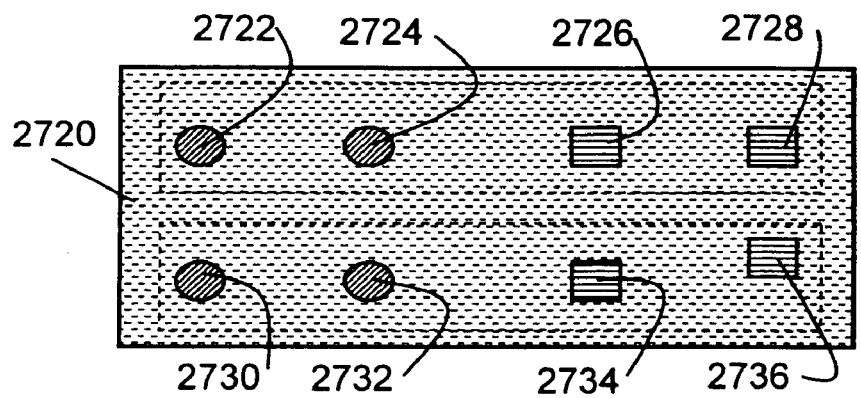

FIGS. 27a and 27b show plan views of sensor patches according to further embodiments of the invention. FIG. 27a shows patch 2700 including two transmitters 2702 and 2704 and two receivers 2706 and 2708. Using this arrangement, a total of four different pathways can be established within the underlying tissues. FIG. 27b shows a sensor patch 2720 having four transmitters 2722, 2724, 2730 and 2732 and four receivers 2726, 2728, 2734 and 2736. Using this arrangement, a total of 16 different pathways can be established within the underlying tissues. Also, in addition to different pathway depths due to the different transmitter/receiver spacings, the arrangements shown in FIGS. 27a and 27b can provide different pathway locations without need to re-position the patch on the patient's skin or other tissue boundary.

Figure 28:
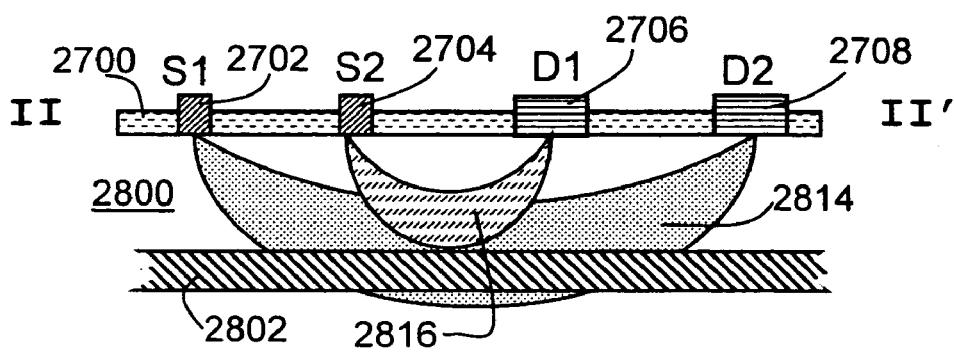
FIG. 28 is a cross section along II-II' of the sensor patch of FIG. 27a placed on tissues containing a blood vessel of interest, according to an embodiment of the invention.

FIG. 28 shows a cross section along II-II' of the sensor patch of FIG. 27a placed on tissues containing a blood vessel of interest, according to an embodiment of the invention. Two exemplary pathways 2816 and 2814 are shown within tissues 2800. As shown, pathway 2816 does not include blood vessel 2802, and pathway 2814 includes blood vessel 2802.

Figure 29:
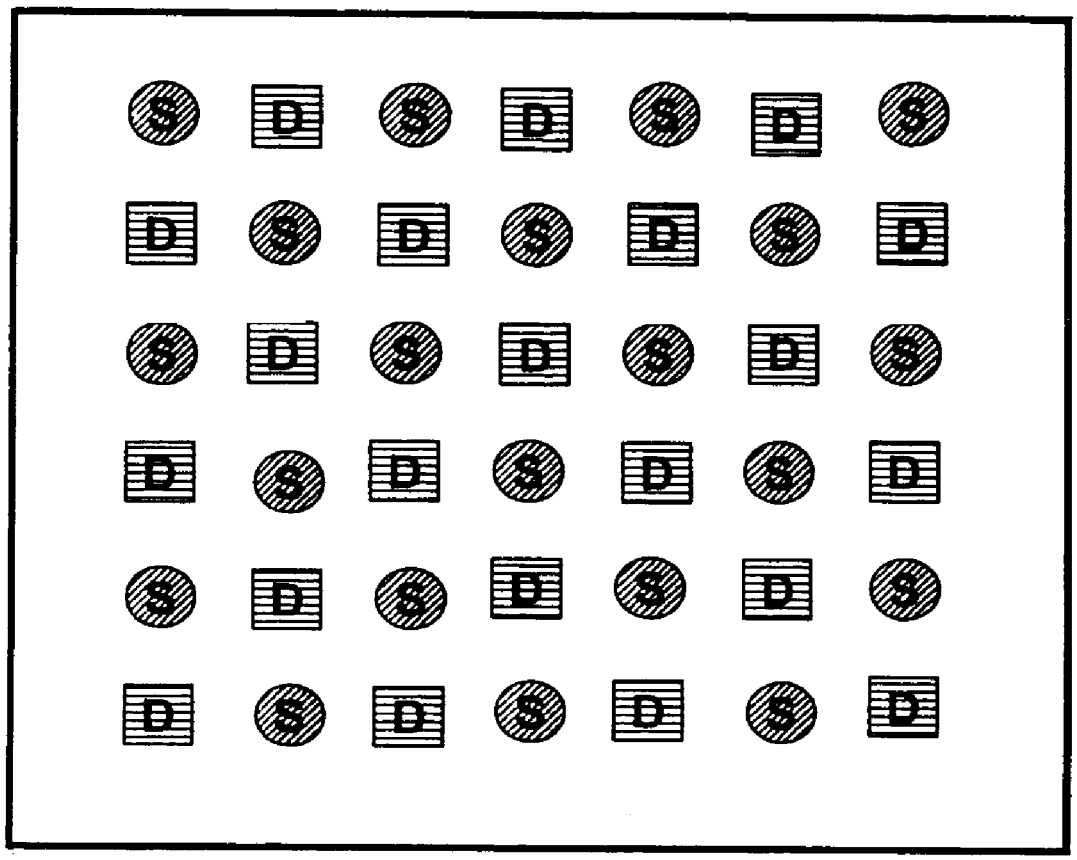
FIG. 29 is a plan view of a sensor patch having an array of transmitters and receivers, according to an embodiment of the invention.

FIG. 29 shows a plan view of a sensor patch having an array of transmitters and receivers, according to an embodiment of the invention. The sensor patch of FIG. 29 includes 21 transmitters, shown as the circles marked "S", and 21 receivers, shown as the squares marked "D". An array arrangement as shown in FIG. 29 has a number of advantages over smaller sensor patches such as shown FIGS. 25a and 25b, including repositioning the effective pathways without detaching the patch from the skin or tissue boundary, mapping or imaging to more precisely locate structures within the tissues (such as large veins and arteries), providing several different depths through the great many transmitter-receiver spacings. For example, if an array-type sensor patch is used over several days on adhered to a patient's neck, the array will be able to adjust itself to accommodate different neck positions which may cause shifting of the position of the internal jugular vein relative to the sensor patch. The sensor patch of FIG. 29 can be made of launch optics and collecting optics and optical fibers as shown and described in FIG. 22. Alternatively, CCD technology, or custom made silicon photo detector and laser diode arrays could be used. In general greater numbers of transmitter and receiver sites will provide better imaging and freedom to choose optimal pairings. For some applications, it has been found that providing at least 10 transmitters and at least 10 receivers is suitable. It has been found that a patch 7 cm×5 cm, having adjacent transmitter/receiver spacing of about 1 cm is suitable for many applications (about 35 transmitters and receivers total). However, higher resolution imaging can be accomplished with the same size patch but with 0.5 cm spacing (about 140 transmitters and receivers total), or even 0.25 cam spacing (about 560 transmitters and receivers) is suitable. Although it is not necessary for equal numbers of transmitters and receivers to be present in an array-type sensor, roughly equal numbers and distributions are preferred for imaging purposes.

Figure 30:
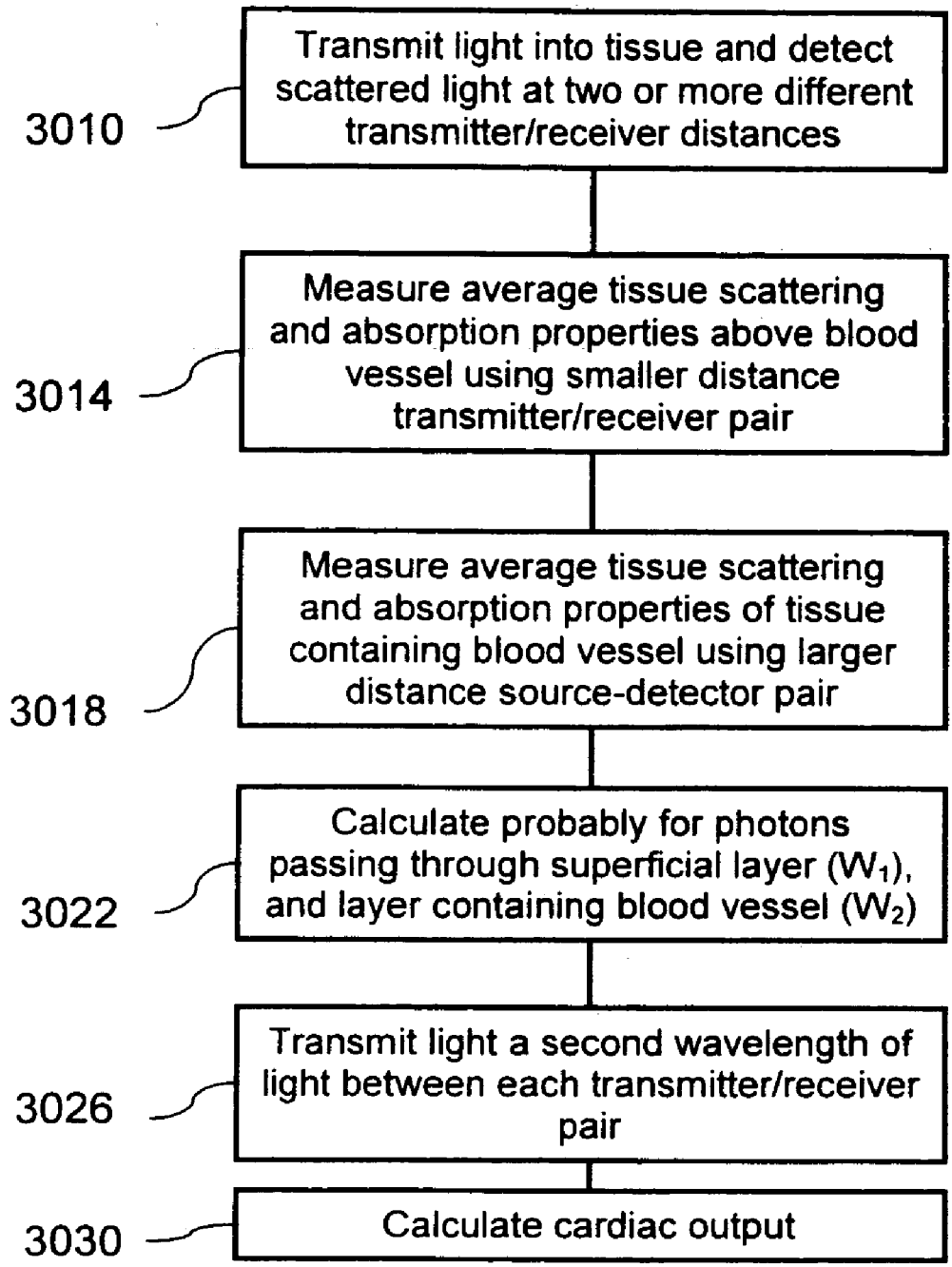
FIG. 30 is a flowchart illustrating several steps relating to measuring cardiac output according to embodiments of the invention.

FIG. 30 is a flowchart illustrating several steps relating to measuring cardiac output according to embodiments of the invention. In step 3010, electromagnetic radiation is transmitted into the patient's tissues at one or more locations and back scattered light is detected or received at one or more locations. The radiation is preferably transmitted and received using the systems and apparatus as shown and described above with respect to FIGS. 21-29. As described above, there should be at least two different pathway depths for the radiation that is detected by one or more receivers. In the embodiments described above, the different depths of the pathways is accomplished by providing different transmitter receiver distances.

In step 3014, the transmitter-receiver, or source-detector pair creating the shallower depth pathway is used to measure the average tissue scattering and absorption properties of the superficial layer above the blood vessel (preferably the internal jugular vein). In the foregoing embodiments shown and described with respect to FIGS. 21, 23, 26 and 28, the shallower or shallowest pathway should substantially exclude the blood vessel of interest (in many cases, the internal jugular vein). In order to provide more accurate calculations for W1, as described below, preferably spatial locations within the blood vessel should have less than about 20% photon probability. Even more preferably, spatial locations within the blood vessel should have less than about 5% probability for photons traveling between the transmitter and receiver pair for the shallowest pathway. Finally, it has been found that in order to further increase the practical applicability and further increase the accuracy for calculations for W1 the photon probability should preferably be less than about 1%.

In step 3018, the transmitter-receiver, source-detector pair creating the deeper depth pathway is used to measure the average tissue scattering and absorption properties of both the superficial tissues as well as the blood vessel of interest.

In step 3022, for the source-detector with large distance, the probably for light to pass through superficial layer ($W_1$) and the layer contains the internal jugular vein ($W_2$) are calculated, preferably through the photon diffusion equation as discussed in further detail below, using the average tissue scattering and absorption properties measured in step 3014. The absorption properties of the layer containing the internal jugular vein can then be calculated through the following relationship:

$$\mu_{a,IJ} = \frac{\overline{\mu}_a - W_1 \cdot \mu_{a,suoerfucuak}}{W_2}$$

As mentioned, the values for $W_1$ and $W_2$ are preferably calculated from photon diffusion equation:

$$-D\nabla^2 \Phi(r, t) + v\mu_a \Phi(r, t) + \frac{\partial \Phi(r, t)}{\partial t} = vS(r, t)$$

where D is the diffusion constant, v is the speed of light, and $\mu_a$ is the absorption coefficient of medium to the light.

The measurements from the transmitter-receiver or source-detector pair having the shorter separation distance, or shallower depth, are used to calculate the probability of photon distribution inside depth from surface to $z_1$ ($z_1$ is typically 2 cm) which is $W_1$.

$$W_1 = \int_0^{z_1} \left[ \int_\infty \int \frac{1}{4\pi D(\vec{r} - \vec{r}_s)} e^{ik(\vec{r} - \vec{r}_s)} \cdot \frac{1}{4\pi D(\vec{r}_d - \vec{r})} e^{ik(\vec{r}_d - \vec{r})} dx dy \right] dz$$

The measurements from the source-detector pair with larger separation distance, or greater depth, are used to calculate the photon probability distribution from depth $z_1$ to $z_2$, which is $W_2$:

$$W_2 = \int_{z_1}^{z_2} \left[ \int_\infty \int \frac{1}{4\pi D(\vec{r} - \vec{r}_s)} e^{ik(\vec{r} - \vec{r}_s)} \cdot \frac{1}{4\pi D(\vec{r}_d - \vec{r})} e^{ik(\vec{r}_d - \vec{r})} dx dy \right] dz$$

where $r_s$ is the position of light source, $r_d$ is the position of detector, and r is the position of a certain position inside medium. K is the wave vector which can be derived from the photon diffusion equation, D is the diffusion constant of medium.

From $W_1$ and $W_2$ and the absorption property of tissue at depth from $z_1$ to $z_2$ can be derived from equation:

$$\mu_{a,IJ} = \frac{\overline{\mu}_{a,depth2} - W_1 \cdot \mu_{a,depth1}}{W_2}$$

In step 3026, steps 3010 through 3022 are repeated for a second wavelength of electromagnetic radiation. Note that the transmission of the second wavelength can be alternated with that of the first wavelength, such that the steps shown in FIG. 30 do not have to be performed in the strict order shown. Preferably, at least two different wavelengths of light between 680 nm to 900 nm are transmitted from each source position to obtain the absorption properties of the internal jugular vein at each wavelength and to calculate blood oxygen saturation. If the absorption properties of the blood (in this example, the internal jugular blood) are obtained at two or more wavelengths then the concentrations of deoxygenated hemoglobin (C_Hb) and oxygenated hemoglobin (C_HbO) can be calculated from:

$$\mu_{a,IJ}{}^\lambda = C_{Hb,IJ}\epsilon_{Hb}{}^\lambda + C_{HbO,IJ}\epsilon_{HbO}{}^\lambda$$

where $\epsilon$ is the pre-determined absorption of deoxygenated hemoglobin (Hb) and oxygenated hemoglobin (HbO) per unit concentration (e.g. grams/liter). The internal jugular blood saturation can then be calculated as:

$$S_{IJ}O_2 = \frac{C_{HbO,IJ}}{C_{HbO,IJ} + C_{HB,IJ}} \%$$

Note that while the present and several of the foregoing embodiments have been described using the example of blood oxygen saturation and cardiac output, the invention is also applicable to monitor other parameters relating to the patient's blood. For example, blood pH can be monitored using met-hemoglobin as a target chromophore, as is described in further detail above. Another example is monitoring water and/or lipid in the blood, using radiation wavelengths where are selected to be suitable for the particular chromophore application.

In step 3030, the oxygen saturation in the blood vessel is then used for calculation of cardiac output, as discussed above with respect to the Fick principle:

$$CadiacOutput = \frac{OxygenConsumption}{(S_aO_2 - S_{IJ}O_2)A}$$

In cases where the blood vessel being monitored is a vein, than $S_aO_2$, the arterial blood oxygen saturation, can measured through conventional methods, for example using pulse oximetry. The value for A can be calculated as described above as [Hb]×1.36 where [Hb] is the blood hemoglobin concentration and 1.36 is a factor subsuming the oxygen carrying capacity of the hemoglobin. The calculation and processing steps described with respect to FIG. 30 are preferably performed in a processor such as in system controller 2215 in FIG. 22 as described above.

According to an alternative embodiment of the invention, The $S_aO_2$ can be measured without using conventional means, such as a standard pulse oximeter. According to this embodiment, $S_aO_2$ is measured through the same patch sensor as shown in FIG. 23 as described above, the amplitudes of the optical signals especially the source-detector pair with largest separation are modulated by the pulsation by the major artery which is adjacent to the internal jugular vein, i.e. the carotid artery. The amplitude of such modulated signals at least two different wavelengths are used to calculate the oxygen saturation of arterial blood, as described above.

Although the above description emphasizes measurement of blood oxygenation for the purpose of determining venous oxygen saturation, cardiac output and pH, the invention is not limited to such applications. The technique described herein can be adapted to selectively probe tissues within the body to measure the level of a particular target chromophore within those tissues and derive diagnostic information about the tissue from the measurement. These measurements can be made in a manner which is accurate, reproducible, precise, fast, operator independent, easy to use, continuous, cost effective, and substantially free of increased mortality and morbidity. Embodiments of the present invention allow measurements that used to be made in a highly invasive manner to be made in a non-invasive or minimally invasive manner. Applications of the technique include measuring the health of a transplanted organ to check for signs of rejection, measuring the perfusion of a skin graft in, for example a burn victim, to determine the health of the graft, potential ambulatory monitoring of high-risk cardiovascular patients, and ambulatory monitoring of high-risk pregnancies.

Figure 31A:
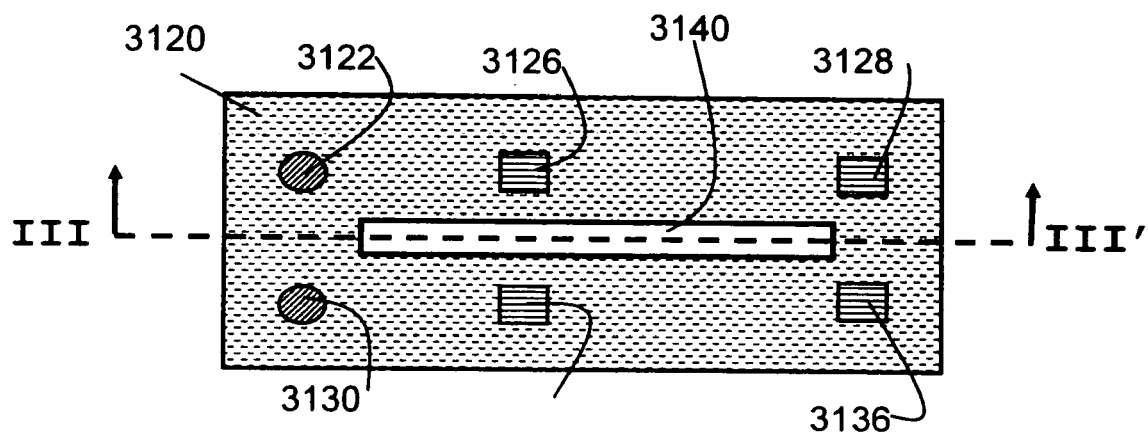
FIGS. 31a and 31b is a sensor patch according to a further embodiment of the invention.
Figure 31B:
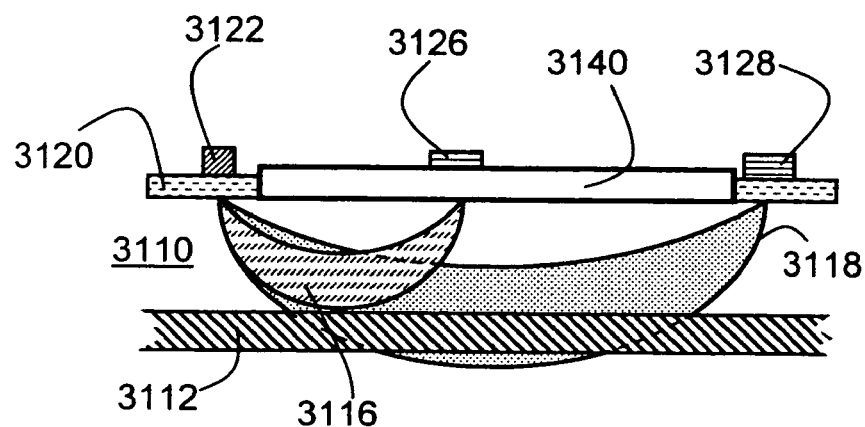

FIGS. 31a and 31b show a sensor patch according to a further embodiment of the invention. FIG. 31a shows sensor patch 3120 that includes two electromagnetic transmitters 3122 and 3130, four electromagnetic receivers 3126, 3128, 3134 and 3136. These structures are identical or similar to those shown and described above, such as, for example, FIGS. 25a, 25b, 27a and 27b. Additionally, sensor patch 3120 includes ultrasonic transducer 3140, which can be similar or identical to the ultrasonic transducer 206 as shown and described, for example, with respect to FIGS. 2A and 2B. Ultrasonic transducer 3140 is coupled to and ultrasound source (not shown). FIG. 31b is a cross-section of the patch 3120 along III-III' in FIG. 31a. As shown, the transmitter-receiver pairs 3122-2126 and 3122-3128 generate electromagnetic radiation pathways 3116 and 3118 respectively. Ultrasonic transducer 3140 is positioned as shown to be used to both image the underlying tissues 3110, for example to precisely locate blood vessel 3112, and to modulate the blood vessel 3112 to provide for more accurate measurement, as described further below.

Figure 32:
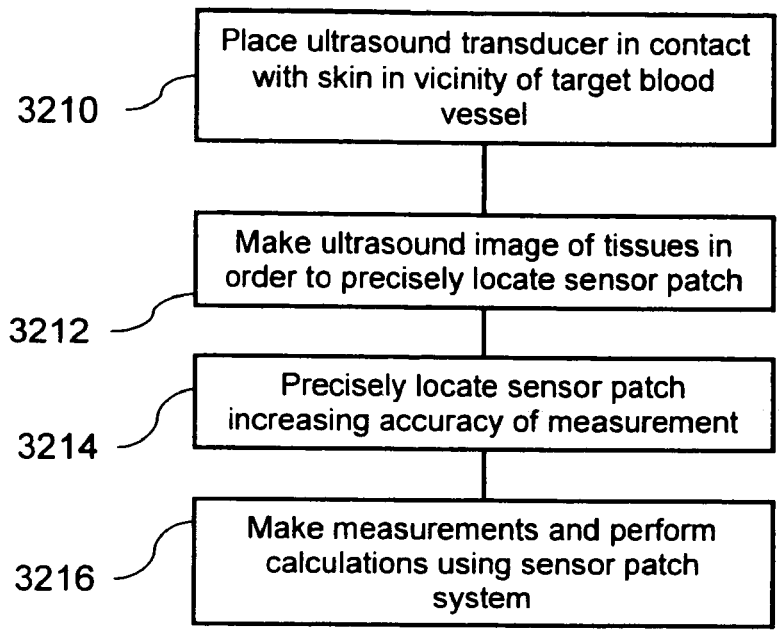
FIG. 32 shows steps involved in monitoring oxygenation and cardiac output according to a further embodiment of the invention.

FIG. 32 shows steps involved monitoring oxygenation and cardiac output according to a further embodiment of the invention. In step 3210, and ultrasound transducer is placed in contact with the patient's skin in the vicinity of the blood vessel of interest. The ultrasound transducer in this embodiment can be of the type integrated into the sensor patch as shown and described in FIGS. 31a and 31b, however, the transducer may also be of the conventional ultrasound imaging type transducer. In step 3212 the ultrasound transducer is used to make images of the issues beneath the skin to precisely locate the target blood vessel. A suitable mark is made on the skin. In step 3214, the optical sensor patch, such as shown in FIGS. 21, 23, and 25-29 is then accurately placed on the patient's skin using the mark such that the electromagnetic pathways are well positioned for accurate measurements. In step 3216, the measurements and calculations are made, such as shown and described with respect to FIG. 30 above.

Figure 33:
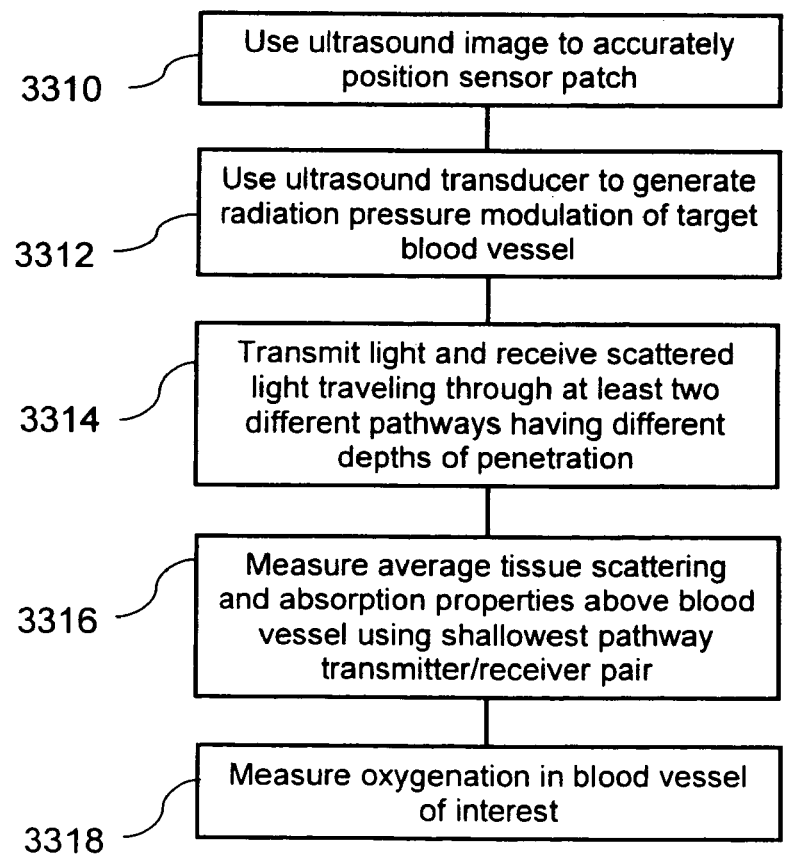
FIG. 33 shows steps involved in monitoring oxygenation and cardiac output according to a further embodiment of the invention.

FIG. 33 shows steps involved in monitoring oxygenation and cardiac output according to a further embodiment of the invention. In step 3310, ultrasound imaging is used to accurately position the sensor patch on the patient's skin, as described with respect to FIG. 32. According to this embodiment, a sensor patch having an integrated ultrasound transducer, such as shown and described with respect to FIGS. 31a and 31b is used. In step 3312, the integrated ultrasound transducer is used to generate radiation pressure modulations in the target blood vessel. In step 3314, electromagnetic radiation is transmitted and received through at least two transmitter-receiver pairs to provide at least two different pathways having different depths of penetration. In step 3316, the average tissue scattering and absorption properties of the superficial tissues is measured using the measurements from the shallowest pathway, as also described with respect to FIG. 30 above. In step 3318, the sensor data relating to the deeper pathway is processed using processing methods and systems described above using ultrasonic radiation pressure modulation. The calculations for relative oxygenation and for cardiac output can have increased accuracy over prior embodiments since the tissue scatter and absorption properties of the superficial tissues are known, and the ultrasound radiation pressure modulation provides for greater signal to noise ratio.

Figure 34:
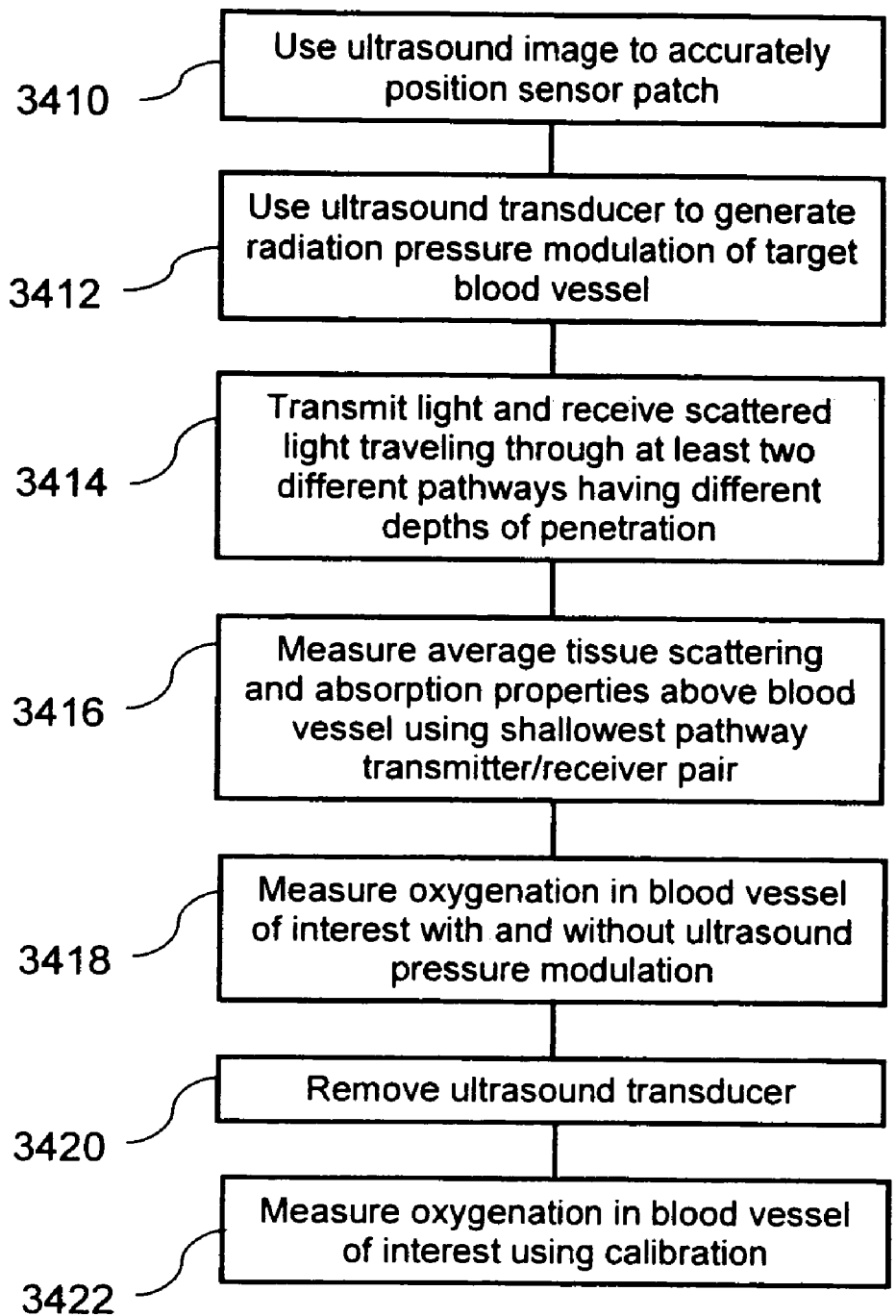
FIG. 34 shows steps involved in monitoring oxygenation and cardiac output according to a further embodiment of the invention.

FIG. 34 shows steps involved in monitoring oxygenation and cardiac output according to a further embodiment of the invention. In step 3410, ultrasound imaging is used to accurately position the sensor patch. In step 3412, the ultrasound transducer is used to generate pressure modulations in the target blood vessel, as in described above. In step 3414, light is transmitted and received through at least two different pathways in the tissues using at least two different transmitter-receiver pairs, as described above. In step 3418, oxygenation in the blood vessel of interest is measured and calculated both with and without the ultrasound radiation pressure modulations. After removing the ultrasound transducer in step 3420, the measurements and/or calculations made without the ultrasound pressure modulations are calibrated or corrected using the measurements made in step 3418. In this way, a combination of ultrasound pressure modulation and multi-depth multi-pathway optical measurements are used to enhance the accuracy of measurement, and allow for increased mobility and duration of the continuous measurement while decreasing the complexity of the system, since the ultrasound system is removed after the initial calibration steps.

Although several of the foregoing embodiments have been described using the internal jugular vein as a target structure for monitoring, there are a number of other target structures within the body that are suitable for blood oxygen monitor using embodiments of the present invention. Several representative example applications will now be described. The exterior jugular vein can be monitored transdermally as shown and described above with respect to FIG. 13. The right subclavian vein, superior vena cava, pulmonary artery and other major blood vessels may be monitored as shown and described above with respect to FIG. 14. Neonatal blood oxygenation can be monitored as shown and described above with respect to FIGS. 18A-18C, and 19. Fetal monitoring can be provided as shown and described above with respect to FIG. 20.

The techniques described are not limited to the hospital or medical office setting. Embodiments of the invention could be made portable and simple to use by virtue of its use of rugged telecom components and low power-consumption devices which could in turn allow its use in ambulances. As shown for example in FIGS. 21 and 22, embodiments of the invention may be useful for real-time monitoring of personnel in high risk situations. For example rescue workers in chemical plants responding to emergencies, or firemen in burning buildings could be monitored remotely for signs of physical distress. Military personnel with ambulatory versions of the sensors could be monitored on the battlefield, and portable versions of the device could be used for first-responder battlefield triage.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A system for monitoring one or more parameters relating to blood of a patient comprising: one or more optical transmitters configured to generate pulsed radiation containing photons having a specific interaction with at least one target chromophore in a target structure within the patient, said one or more optical transmitters configured and positioned to transmit the pulsed radiation from the optical transmitter into at least a first area including a substantial portion of the target structure and into a second area not including a substantial portion of the target structure; one or more optical receivers configured and positioned to detect a portion of the pulsed radiation scattered from at least the first area and the second area; and a processor configured to estimate the one or more parameters relating to the patient's blood, the estimation based in part on the scattered pulsed radiation detected from the first area, and the scattered pulsed radiation from the second area, wherein the processor comprises a central processing unit and a memory device and said one or more optical receivers are configured and adapted to measure optical properties associated with the second area, and wherein said processor is further configured to calculate a probability for the pulsed radiation to pass through the first area and the second area.

2. A system according to claim 1 wherein the target structure is a blood vessel.

3. A system according to claim 1 wherein the second area is selected such that optical properties of tissue in close proximity to the target structure can be estimated.

4. A system according to claim 3 wherein the second area is in close proximity to the target structure.

5. A system according to claim 1 wherein said one or more optical transmitters is adapted to transmit the pulsed radiation into the first and second areas simultaneously.

6. A system according to claim 1 wherein said processor is further adapted to estimate average tissue scattering and absorption properties for the radiation associated with the second area.

7. A system according to claim 1 wherein said probabilities are calculated using a photon diffusion equation.

8. A system according to claim 1 wherein said processor estimates the one or more parameters in part by relating probabilities for the pulsed radiation to pass through the first and second areas.

9. A system according to claim 8 wherein the target structure is a blood vessel and said processor is further adapted to calculate relative blood oxygen saturation in the blood vessel.

10. A system according to claim 1 wherein the pulsed radiation comprises photons having a first wavelength and photons having a second wavelength, the first wavelength selected to have the specific interaction with a first target chromophore, and the second wavelength selected to have a specific interaction with a second target chromophore.

11. A system according to claim 10 wherein the first target chromophore is oxy-hemoglobin and the second target chromophore is deoxy-hemoglobin.

12. A system according to claim 11 wherein the target structure is a blood vessel the one or more of the parameters relating to blood includes oxygenation saturation of blood in the blood vessel.

13. A system according to claim 12 wherein the blood vessel is a major vein.

14. A system according to claim 13 wherein the major vein is the internal jugular vein.

15. A system according to claim 13 wherein the one or more optical sources are further adapted and positioned to transmit the pulsed radiation into a third area including a substantial portion of a second target structure, the one or more optical receivers are further configured and positioned to detect pulsed radiation scattered from the third area, and the third target structure is a major artery.

16. A system according to claim 15 further comprising a filter coupled to at least one of the optical receivers, the filter being configured to select pulsed radiation from the third area with a modulation component at the same frequency or at a harmonic frequency of the pulse in the major artery.

17. A system according to claim 12 wherein the blood vessel is a major artery.

18. A system according to claim 1 wherein the one or more of the parameters relating to blood includes the patient's cardiac output.

19. A system according to claim 1 wherein said one or more optical transmitters comprise an optical source and one or more launch optics coupled to the optical source via one or more optical fibers.

20. A system according to claim 19 wherein said one or more optical receivers comprise one or more optical detectors and one or more collecting optics coupled to the one or more optical detectors via one or more optical fibers.

21. A system according to claim 20 wherein said one or more launch optics and said one or more collecting optics are mounted on a sensor patch designed to be engaged to the patient's skin.

22. A system according to claim 20 further comprising two or more transmitter-receiver pairs each pair comprising one launch optic and one collecting optic, including a first pair having a spacing and position such that the launch optic and collecting optic associated with the first pair transmits pulsed radiation into and detects pulsed radiation scattered from the first area, and a second pair having a spacing and position such that the launch optic and collecting optic associated with the second pair transmits pulsed radiation into and detects pulsed radiation scattered from the second area.

23. A system according to claim 22 wherein the first pair has a spacing between the launch optic and collecting optic of between about 3 cm and about 7 cm, and the second pair has a spacing between the lunch optic and collecting optic of between about 0.5 cm and about 3 cm.

24. A system according to claim 20 wherein said processor comprises a general purpose computer, and said optical source, said system further comprising a system box in which said one or more optical detectors, and said processor are housed, and said box station is in communication with a display adapted to display the one or more parameters relating to blood to a human operator.

25. A system according to claim 20 wherein said processor comprises a portable general purpose computer, said system further comprising a portable box in which said optical source, said one or more optical detectors, and said processor are housed, said portable box being dimensioned and sized such the patient can carry the portable box for extended periods, and said portable box further housing a battery and a wireless transmitter for data communication to a station box located at a hospital or clinic.

26. A system according to claim 1 wherein the one or more optical transmitters are adapted and positioned to transmit the pulsed radiation into the patient at least 10 locations and the one or more optical receivers is adapted and positioned to detect scattered pulsed radiation from the patient at least 10 locations.

27. A system according to claim 26 wherein the optical transmitters and receivers are used to generate an image of tissues with the patient.

28. A system according to claim 26 wherein pairs of transmitter and receiver locations are selected dynamically in order to provide improved monitoring of the one or more parameters relating to blood.

29. A system according to claim 1 further comprising an ultrasound transducer configured to transmit ultrasound radiation into the patient at locations including the first area and the target structure.

30. A system according to claim 29 wherein the ultrasound transducer is adapted to generate an image of tissues within the first area including the target structure to enable placement of the one or more optical transmitters and the one more optical receivers on the patient so as to enhance the accuracy of the monitoring of the system.

31. A system according to claim 29 wherein the ultrasound transducer is configured to provide an ultrasound radiation pressure field to modulate the target structure at a modulation frequency, and the system further comprising a filter coupled to at least one of the optical detectors, the filter being configured to select detected photons with a modulation component at the same frequency as the modulation frequency of the radiation pressure modulation field, or at a harmonic of the modulation frequency.

32. A system according to claim 31 wherein the processor is adapted to calculate a calibration adjustment based on measurements performed by the one or more optical receivers both with and without the use of the ultrasound transducer and the filter.

33. A system according to claim 1 wherein the one or more parameters relating to blood is blood pH level, and one of the at least one target chromophores is met-hemoglobin.

34. A system according to claim 1 wherein the one or more parameters relating to blood relates to water or lipid concentrations in the blood.

35. A system according to claim 1 wherein the target structure is selected from a set consisting of exterior jugular vein, subclavian vein, superior vena cava and pulmonary artery.

36. A system according to claim 1 wherein the patient is a neonatal patient.

37. A system according to claim 1 wherein the patient is a fetus.

38. A system according to claim 1 wherein the second area has a depth of at least 1 cm from a tissue boundary.

39. A system according to claim 38 wherein the target structure is located about 2 cm from a tissue boundary of the patient.

40. A system according to claim 1 wherein the second area excludes portions of the target structure having a 20% or greater photon probability for photon generated by the one or more optical transmitters when transmitting into the second area.

41. A system according to claim 40 wherein the second area excludes portions of the target structure having a 5% or greater photon probability for photon generated by the one or more optical transmitters when transmitting into the second area.

42. A system according to claim 41 wherein the second area excludes portions of the target structure having a 1% or greater photon probability for photon generated by the one or more optical transmitters when transmitting into the second area.

43. A method for monitoring one or more parameters relating to blood of a patient comprising the steps of: engaging one or more optical transmitters and one or more optical receivers on a tissue boundary of the patient; generating pulsed radiation containing photons having a specific interaction with at least one target chromophore in a target structure within the patient; transmitting said pulsed radiation through the optical transmitters into a first area including a substantial portion of a target blood vessel and into a second area not including a substantial portion of the target structure; detecting with the one or more optical receivers a portion of the pulsed radiation scattered from at least the first area and the second area; estimating the one or more parameters relating to a patient's blood based in part on the detected scattered pulsed radiation from the first area, and the scattered pulsed radiation from the second area; and calculating optical properties associated with the second area, wherein said step of estimating is based in part on the measured optical properties associated with the second area, and wherein said step of estimating the one or more parameters includes calculating a probability for the pulsed radiation to pass through the first area and the second area.

44. A method according to claim 43 wherein the target structure is a blood vessel.

45. A method according to claim 43 wherein the second area is selected such that optical properties of tissue in close proximity to the target structure can be estimated.

46. A method according to claim 43 wherein said one or more optical transmitters is adapted to transmit the pulsed radiation into the first and second areas simultaneously.

47. A method according to claim 43 wherein said optical properties associated with the second area includes average tissue scattering and absorption properties for the pulsed radiation associated with the second area.

48. A method according to claim 43 wherein said probabilities are calculated using a photon diffusion equation.

49. A method according to claim 43 wherein the target structure is a blood vessel and said step of estimating the one or more parameters comprises calculating relative blood oxygen saturation in the blood vessel.

50. A method according to claim 43 wherein the pulsed radiation comprises photons having a first wavelength and photons having a second wavelength, the first wavelength selected to have the specific interaction with the target chromophore, and the second wavelength selected to have a specific interaction with a second target chromophore.

51. A method according to claim 50 wherein the target chromophore is oxy-hemoglobin and the second target chromophore is deoxy-hemoglobin.

52. A method according to claim 50 wherein the target structure is a blood vessel the one or more of the parameters relating to blood includes oxygenation saturation of blood in the blood vessel.

53. A method according to claim 43 wherein the one or more parameters relating to blood is blood pH level, and one of the at least one target chromophores is met-hemoglobin.

54. A method according to claim 43 wherein the target structure comprises an internal jugular vein, and the tissue interface is neck skin of the patient.

55. A method according to claim 43 wherein the target structure is selected from a set consisting of exterior jugular vein, subclavian vein, superior vena cava and pulmonary artery.

56. A method according to claim 43 wherein the patient is a neonatal patient.

57. A method according to claim 43 wherein the patient is a fetus.

58. A method according to claim 43 wherein the step of transmitting said pulsed radiation includes transmitting the pulsed radiation through the optical transmitters into a third area including a substantial portion of a second target structure, and said step of detecting comprises detecting pulsed radiation scattered from the third area.

59. A method according to claim 58 wherein the second target area is an artery and the method further comprises the step of filtering radiation detected from the third area with a modulation component at the same frequency or at a harmonic frequency of the pulse in the artery.

60. A method according to claim 43 wherein the one or more of the parameters relating to blood includes the patient's cardiac output.

61. A method according to claim 43 wherein said step of generating pulsed radiation uses at least one optical source, said step of transmitting uses one or more launch optics coupled to the at least one optical source via one or more optical fibers, said one or more optical receivers comprise one or more optical detectors and one or more collecting optics coupled to the one or more optical detectors via one or more optical fibers.

62. A method according to claim 61 wherein the tissue boundary is the patient's skin, said one or more launch optics and said one or more collecting optics are mounted on a sensor patch designed to be engaged to the patient's skin, and said step of engaging includes engaging the sensor patch onto the patient's skin.

63. A method according to claim 62 wherein said steps of transmitting and detecting use a first transmitter-receiver pair have a spacing and position such that the launch optic and collecting optic associated with the first pair transmits pulsed radiation into and detects pulsed radiation scattered from the first area, and a second transmitter-receiver pair having a spacing and position such that the launch optic and collecting optic associated with the second pair transmits pulsed radiation into and detects pulsed radiation scattered from the second area.

64. A method according to claim 63 wherein the first pair has a spacing between the launch optic and collecting optic of between about 3 cm and about 7 cm, and the second pair has a spacing between the launch optic and collecting optic of between about 0.5 cm and about 3 cm.

65. A method according to claim 43 further comprising the step displaying to a human operator the estimated one or more parameters relating to blood.

66. A method according to claim 43 further comprising the steps of: recording data, calculations and estimates on a memory housed within a portable unit, said portable unit being dimensioned and sized such that the patient can carry the portable unit for extended periods; and wirelessly transmitting data relating to the one or more parameters to a station box located at a hospital or clinic.

67. A method according to claim 43 wherein the one or more optical transmitters are adapted and positioned to transmit the pulsed radiation into the patient at least 10 locations and the one or more optical receivers is adapted and positioned to detect scattered pulsed radiation from the patient at least 10 locations.

68. A method according to claim 67 wherein the optical transmitters and receivers are used to generate an image of tissues with the patient.

69. A method according to claim 68 further comprising the step of dynamically selecting pairs of transmitter and receiver locations in order to provide improved monitoring of the one or more parameters relating to blood.

70. A method according to claim 43 further comprising the step of transmitting ultrasound radiation into the patient at locations including the first area and the target structure using an ultrasound transducer.

71. A method according to claim 70 further comprising the step of generating an image of tissues within the first area including the target structure, wherein the step of engaging uses the generated image of tissues in order to place the one or more optical transmitters and the one more optical receivers on the tissue boundary of the patient so as to enhance the accuracy of the monitoring of the system.

72. A method according to claim 70 further comprising the steps of: generating an ultrasound radiation pressure field to modulate the target structure at a modulation frequency; and filtering detected photons with a modulation component at the same frequency as the modulation frequency of the radiation pressure modulation field, or at a harmonic of the modulation frequency.

* * * * *